(12) United States Patent
Zigdon

(10) Patent No.: US 12,350,220 B2
(45) Date of Patent: Jul. 8, 2025

(54) MEDICAL ADULT TOY

(71) Applicant: ZIGI CARMEL INITIATIVES & INVESTMENTS LTD, Tel Aviv (IL)

(72) Inventor: Carmel Zigdon, Givatayim (IL)

(73) Assignee: ZIGI CARMEL INITIATIVES & INVESTMENTS LTD, Tel Aviv (IL)

( * ) Notice: Subject to any disclaimer, the term of this patent is extended or adjusted under 35 U.S.C. 154(b) by 0 days.

(21) Appl. No.: 18/567,766

(22) PCT Filed: Jul. 20, 2022

(86) PCT No.: PCT/IL2022/050783
§ 371 (c)(1),
(2) Date: Dec. 6, 2023

(87) PCT Pub. No.: WO2023/002485
PCT Pub. Date: Jan. 26, 2023

(65) Prior Publication Data
US 2024/0207133 A1 Jun. 27, 2024

Related U.S. Application Data

(60) Provisional application No. 63/223,822, filed on Jul. 20, 2021.

(51) Int. Cl.
*A61H 19/00* (2006.01)
(52) U.S. Cl.
CPC ......... *A61H 19/44* (2013.01); *A61H 2201/50* (2013.01)

(58) Field of Classification Search
CPC .............. A61H 19/44; A61H 19/40; A61H 2201/0107; A61H 2201/105; A61H 23/00; A61H 19/34; A61H 19/50
See application file for complete search history.

(56) References Cited

U.S. PATENT DOCUMENTS

| | | |
|---|---|---|
| 2009/0171144 A1 | 7/2009 | Squicciarini |
| 2009/0216076 A1 | 8/2009 | Kain |
| 2014/0148740 A1 | 5/2014 | Howsam |
| 2014/0171734 A1* | 6/2014 | Kassman ............... A61H 19/32 600/38 |
| 2017/0087049 A1 | 3/2017 | Hutchison |

(Continued)

FOREIGN PATENT DOCUMENTS

| | | |
|---|---|---|
| CN | 103830086 A | 6/2014 |
| CN | 107307987 A | 11/2017 |
| CN | 208756486 U | 4/2019 |

(Continued)

OTHER PUBLICATIONS

Sep. 22, 2022 International Search Report issued on International Application No. PCT/IL2022/050783.

(Continued)

*Primary Examiner* — Christine H Matthews
(74) *Attorney, Agent, or Firm* — Whitestone Law, PLLC

(57) ABSTRACT

Some embodiments relate to an adult toy including a head port configured for removably attaching thereto one or more operative heads, each operative head comprising at least one operational unit. A motor can be associated with the head port, the motor being configured to be operationally coupled to the operational unit of each of the operative heads for facilitating performance of operation thereof.

10 Claims, 32 Drawing Sheets

(56) References Cited

U.S. PATENT DOCUMENTS

2017/0189263 A1* 7/2017 Cambridge ............ A61H 19/40

FOREIGN PATENT DOCUMENTS

| CN | 110279678 B | 9/2019 |
|---|---|---|
| CN | 306406985 S | 3/2021 |
| CN | 213596271 U | 7/2021 |
| CN | 306740885 S | 8/2021 |
| CN | 113848242 A | 12/2021 |
| CN | 307284907 S | 4/2022 |
| CN | 115052587 A | 9/2022 |
| WO | 2013138658 A1 | 9/2013 |

OTHER PUBLICATIONS

Sep. 28, 2022 Written Opinion of the International Searching Authority issued on International Application No. PCT/IL2022/050783.

Israel Cart; IKOKY 2 In 1 Dildo Vibrator Anal Bead; (Oct. 14, 2019). [online] . [Retrieved on Aug. 3, 2022] . Retrieved from the Internet. URL: https://israel-cart. com /products/ikoky- 2-in- 1-dildo-vibrator-anal-bead-vagina-cli toris-anus-stimulator-g-spot-massage-360-degree-rotation-sex-toys-for-women (Dating is based on Google Search) Israel Cart (Oct. 14, 2019).

The Hemp Pharmacist;Ananda Bliss Intimate Oil; (Oct. 18, 2019). [online]. [Retrieved on Aug. 8, 2022]. Retrieved from the Internet. URL: https:// thehemppharmacist.com/producUbliss-intimacy-oil/ (Dating is based on Google Search) The Hemp Pharmacist (Oct. 18, 2019).

Vimeo.; Womanizer Duo Unboxing Experience; (Mar. 4, 2021). [online]. [Retrieved on Sep. 21, 2022]. Retrieved from the Internet. URL: https://www.bing.com/videos/search?q=Womanizer+Duo&docid=608040367406671633&mid=54BF430AF05CFD7CF10F54BF430AF05CFD7Ci:;10F&view=detail&FOR•=VIRE (Dating is based on Google Search) Vimeo (Apr. 3, 2021).

Bondara.; Toygasm 8 Function 3-in-I Licking Pussy Pump Vibrator; (Oct. 18, 2019). [online]. [Retrieved on Sep. 21, 2022]. Retrieved from the Internet. URL: https:// www.bondara.co .uk/bondara-toygasm-8-function-3-inl -licking-pussy-pump-vibrator (Dating is based on Google Search) Bondara (Oct. 18, 2019).

\* cited by examiner

MEDICAL ADULT TOY

CROSS-REFERENCE TO RELATED APPLICATIONS

This application is a national phase filing under 35 C.F.R. § 371 of and claims priority to PCT Patent Application No. PCT/IL2022/050783, filed on Jul. 20, 2022, which claims the priority benefit under 35 U.S.C. § 119 of U.S. Patent Application No. 63/223,822, filed on Jul. 20, 2021, the contents of each of which are hereby incorporated in their entireties by reference.

TECHNICAL FIELD

The presently disclosed subject matter relates to adult toys, and more particularly to medical adult toys that can perform various operations with user organs and deliver stimulating and medical substances, such as cannabinoid extracts.

BACKGROUND

Intimate lifestyle products (interchangeably referred to herein as adult toys or adult sex toys) are used to stimulate vagina, clitoris, anal cavity or other sexual organs for the purposes of sexual pleasure. The sexual pleasure depends on the usability of these products and the operations they can perform with respect to the sexual organs. The use of intimate lifestyle products may require the use of lubricants. These lubricants may increase stimulation or sensation. There are various known shapes of the adult toys. It is known that dispensing of certain sexual stimulating substances such as liquids containing a sex steroid or a cannabinoid may have a stimulating effect on female sexual desire and receptivity. With the legalization of both medical and recreational marijuana in some countries and a few US states, its use has become more widely prevalent thereby raising a need for new adult toys configured to stimulate the female sex organ in different manners and dispensing cannabinoid substance for stimulating sexual satisfaction and treating various medical conditions in females and males.

SUMMARY

The presently disclosed subject matter relates to adult toys that provide increased pleasure to a user thereof. In addition to the sexual pleasure, the adult toys disclosed herein provide medicinal relief from sexual and mental problems including problems with ability to have an intercourse such as: anxiety and physical pain. The adult toys disclosed herein deliver (dispense) a lubricant, such a sexually stimulating substance at the sexual organs of the user. The lubricant is a cannabinoid extract, and more particularly CBD and/or THC oil. The euphoric high associated with THC helps to slow things down, and to intensify feelings of sexual pleasure. The CBD oil is known to reduced discomfort, enhance sensations, reduce pain, and ease stress and anxiety. For example, different researches suggest that CBD is able to lower inflammation by affecting the body's activity with endocannabinoid receptors. This includes both chronic and acute inflammation. The CBD oil can handle various medical conditions, such as: vulvodynia, veganism's, vaginal scarring, pelvic floor dysfunction, uterine fibroids, ovarian cysts, interstitial cystitis. The adult toys disclosed herein, in addition to providing sexual stimulation at the sex organs, provide these lubricants at the sex organs to enhance the pleasure and/or relief for which the adult toy is being used by the user. In addition, the adult toys have mechanisms to heat the lubricants prior to its delivery for further enhancing the pleasure and/or relief.

According to a first aspect of the presently disclosed subject matter there is provided an adult toy including: a head port configured for removably attaching thereto one or more operative heads, each operative head including at least one operational unit; and a motor associated with the head port, said motor being configured to be operationally coupled to the operational unit of each of the operative heads for facilitating performance of operation thereof. The adult toy can further include a controller configured for operating said motor.

The head port can be configured for removably attaching the operative heads by an attaching action and the motor can be configured to be operationally coupled to the corresponding operational units during said attaching action. The attaching action includes a snap attachment. The head port can extend along a longitudinal axis, and the head port can be configured for removably attaching thereto the operative heads along said longitudinal axis. The attaching action can include pressing the operative head on to the head port along said longitudinal axis and the attachment can be effected by virtue of the corresponding dimensions of the head port and the operative head.

The head port can include a lubricant delivery port configured for delivering a lubricant therethrough. The lubricant delivery port can be configured for connecting thereto a lubricant port extension element of the operative heads, and for delivering said lubricant through the lubricant port extension element when said operative head is attached to the head port. The lubricant delivery port is configured for connecting thereto the lubricant port extension element in a leak-proof manner. In some examples, the connection between the lubricant delivery port and the lubricant port extension element can include a sealing member. The lubricant port can be configured for connecting thereto the lubricant port extension element of the operative head during said attaching action.

In some examples, the adult toy can further include a main head port configured for attaching thereto a main head having a main operational unit. In some examples, the main head can constitute a part of the adult toy and can be fixed attached at the main head port. In other examples, the main head port can be configured for removably attaching thereto one or more main heads including said main head. The one or main heads can include different operational units such as vibration units. The different main heads can have different shape, size, textures, etc for providing different sensations at the sexual organ of the user.

The main head port can extend along a main longitudinal axis, and the main head port is configured for attaching thereto the main head along said main longitudinal axis, for example by pressing on to the main head port along the main longitudinal axis. In such examples, the longitudinal axis of the head port described above constitutes an auxiliary longitudinal axis.

In the examples in which the adult toy includes the main head port, the head port described above can be an auxiliary head port and the operative heads can include auxiliary heads, each of the operational units being an auxiliary operational unit.

The adult toy can further include a main lubricant delivery port extending through the main head port and configured for delivering a lubricant therethrough, and in such examples, the lubricant delivery port described above constitutes an auxiliary lubricant delivery port.

The main longitudinal axis and the auxiliary longitudinal axis can be disposed at an acute angle therebetween, and the angle between the main longitudinal axis and the auxiliary longitudinal axis can be such that when the main head and the auxiliary head are attached to the corresponding head port, the main head can interact with vagina and the auxiliary head can simultaneously interact with clitoris of a user of the adult toy. For instance, the main head can be insertable into the vagina while the auxiliary head interacts with the clitoris externally.

In some examples, the adult toy can further include a main motor configured to be operationally coupled to the main operative unit for facilitating performance of operation thereof. The main operative unit can be a vibrator unit. In such examples, the motor described above constitutes an auxiliary motor. The controller can be configured for operating said main motor. The controller can be configured to operate the main motor in coordination with the auxiliary motor. The controller can be configured to operate the main motor and the auxiliary motor according to a predetermined pattern, thereby synchronizing the operations of the main operational unit and auxiliary operational unit. The controller can be configured to operate the main motor independently of the auxiliary motor. In some examples, the adult toy can include separate controllers constituting parts of same or different controlling units to operate the main the auxiliary motor respectively.

According to a second aspect of the presently disclosed subject matter there is provided an operative head for use with an adult toy including a head port for removably attaching thereto the operative head, and a motor, said operative head including: an operational unit configured to be operationally coupled to said motor for performing a corresponding operation; said operative head being configured to be removably attached to the head port.

The operative head can be configured to be removably attached to the head port by an attaching action and the operational unit is configured to be operationally coupled to the motor during said attaching action. The attaching action can include a snap attachment. The attaching action can be same or similar to the attaching action described above with respect to the first aspect of the presently disclosed subject matter.

The operative head can include a lubricant port extension element configured for delivering a lubricant therethrough proximal to the operational unit. In some examples, the lubricant port extension element can be configured to deliver the lubricant at the operational unit. In other examples, the lubricant port extension element can be configured to deliver the lubricant at the sexual organ of the user. The lubricant port extension element can be configured to be connected to a lubricant delivery port constituting a part of the head port of the adult toy, and to deliver said lubricant from the lubricant delivery port to a user of the adult toy. The lubricant port extension element can be configured to be connected to the lubricant delivery port in a leak-proof manner, and in some examples the connection can include a sealing member. The lubricant port extension element can be configured to be connected to the lubricant delivery port during said attaching action.

Optionally, the operative head can be a vibration head and the operational unit can be a vibrator unit, and the operative head can include a vibrator motor configured to be operationally coupled to said motor for performing the operation of vibration.

Optionally, the operative head can be a suction head and the operational unit can be a suction unit, and the operative head can include a suction pump configured to be operationally coupled to said motor for performing the operation of suction.

Optionally, the operative head can be a licking head and the operational unit can be a licking-mimicking unit. The licking-mimicking unit can mimic a licking action the clitoris of the user. The operative head can include a licking element configured to be moved by a licking motor arrangement, thereby mimicking a licking effect, said licking motor arrangement can be configured to be operationally coupled to said motor for performing the operation of licking-mimicking. In some examples, the licking element can be a licking ball housed in a ball housing, said housing can be configured to be rotated by the licking motor. In other examples, the licking element can be configured to be rotated about a rotation axis by the licking motor. In such examples, the licking element can be a ball.

The operative head can be configured to interact with, or even contact, a clitoris of a user of the adult toy, at least when the operative head is attached to the head port. The operational unit is configured to perform said operation with respect to the clitoris. The operation can include causing a vibration effect, touching, rubbing, pulling a membrane (for example, the suction), or causing any sensation at the clitoris. The lubricant port extension element is configured to deliver said lubricant at the clitoris.

According to a third aspect of the presently disclosed subject matter there is provided an adult toy including: a lubricant inlet port connectable to a lubricant source containing a lubricant to be delivered through the adult toy; a main conduit configured to deliver said lubricant from the lubricant inlet port through a main lubricant delivery port; an auxiliary conduit configured to deliver said lubricant from the lubricant inlet port through an auxiliary lubricant delivery port distant from the main lubricant delivery port; and a pumping mechanism for pumping the lubricant from the lubricant inlet port through each of the main conduit and auxiliary conduit.

The lubricant inlet port is a double one-way valve, or a valve having two one-way liquid pathways extending therefrom. The pumping mechanism can include a first peristaltic pump configured to pump the lubricant from said lubricant inlet port through the main conduit, and a second peristaltic pump configured to pump the lubricant from said lubricant inlet port through the auxiliary conduit. The main lubricant delivery port can be associated with a main head port of the adult toy configured for attaching thereto main head insertable into a vagina of a user of the adult toy, said main lubricant delivery port being configured to deliver said lubricant through the main head inside the vagina. The auxiliary lubricant delivery port can be associated with an auxiliary head port of the adult toy configured for removably attaching thereto one or more auxiliary heads, each auxiliary head being configured to perform one or more operations associated with a clitoris of a user of the adult toy. The auxiliary lubricant delivery port can be configured for attaching thereto a lubricant port extension element of the corresponding auxiliary head for delivering therethrough the lubricant to the clitoris.

The adult toy can further include a controller configured for controlling the pumping mechanism. In some examples, the controller can be configured to operate the first and the second peristaltic pumps in coordination with each other. In other examples, the controller can be configured to operate the first and the second peristaltic pumps independently of each other.

According to a fourth aspect of the presently disclosed subject matter there is provided an adult toy including: a capsule receiving portion configured for receiving therewithin a lubricant capsule including a lubricant to be delivered through the adult toy; a lubricant inlet port configured to be in fluid communication with said lubricant capsule when positioned in the capsule receiving portion; and a locking mechanism configured for locking the lubricant capsule within the capsule receiving portion, said capsule receiving portion, lubricant inlet port, and locking mechanism being configured to establish said fluid communication during a locking action of the locking mechanism.

The lubricant inlet port and the locking mechanism are so positioned that the locking action causes the engagement of the lubricant inlet port with the lubricant capsule for establishing said fluid communication. The adult toy can further include a connector section, said capsule receiving portion being configured to be removably connected to the connector section, wherein the lubricant inlet port and at least a part of the locking mechanism are positioned at the connector section. The connection of the capsule receiving portion, with the lubricant capsule positioned therewithin, at the connector section via the locking mechanism can cause the engagement between the lubricant inlet port and the lubricant capsule. The lubricant inlet port can include conical end configured to pierce a pierceable portion of the lubricant capsule during said connection. The capsule receiving portion can be configured to receive therewithin the lubricant capsule in a manner so that the pierceable portion faces the lubricant inlet port.

According to a fifth aspect of the presently disclosed subject matter there is provided an adult toy configured for delivering a lubricant therethrough during use of the adult toy, said adult toy including a heating mechanism configured to heat the lubricant prior to said delivery. The lubricant can be a cannabinoid extract, can include CBD oil and/or THC oil.

The lubricant can be contained in a lubricant capsule removably positioned within a capsule receiving portion of the adult toy. The adult toy can further include a locking mechanism configured to lock the lubricant capsule within the capsule receiving portion by a locking action. The heating mechanism can be configured to be activated by at least a part of said locking action. The heating mechanism can be configured to be activated by half of said locking action.

The adult toy can further include a connector section, said capsule receiving portion being configured to be removably connected to the connector section by said locking action, wherein said heating mechanism is at least partially positioned within the capsule receiving portion, said connection of the capsule receiving portion to the connector section competes an electrical circuit for the heating mechanism. The connector section can have a conductor element electrically connected to a power source, and the heating mechanism includes a heating element, said heating element configured to engage the conductor element during said connection of the capsule receiving portion to the connector section to complete said electrical circuit. The power source can be a battery positioned within the adult toy. In some examples, the power source can be an external power source. The adult toy can further include a controller configured to operate the heating mechanism. The adult toy can further include a sensor configured to sense whether the lubricant capsule is positioned within the capsule receiving portion, and the controller can be configured to activate the heating mechanism upon the sensor sensing that the lubricant capsule is positioned within the capsule receiving portion.

It is to be understood herein that the adult toy according to the first aspect can include some or all the features of the adult toy according to any one (or more) of the third, fourth, or fifth aspect. Similarly, the adult toy according to the third aspect can include some or all the features of the adult toy according to any one (or more) of the first, fourth, or fifth aspect. Similarly, the adult toy according to the fourth aspect can include some or all the features of the adult toy according to any one (or more) of the first, third, or fifth aspect. Similarly, the adult toy according to the fifth aspect can include some or all the features of the adult toy according to any one (or more) of the first, third, or fourth aspect.

According to a sixth aspect of the presently disclosed subject matter there is provided an adult toy configured for delivering a cannabinoid extract lubricant to a user therethrough, said adult toy including a capsule receiving portion configured to receive therewithin a lubricant capsule including said cannabinoid extract lubricant.

In some examples, the adult toy can be a male adult toy configured for use by a male user. In other examples, the adult can be configured for use by a female, transgender, gay, or a lesbian user. In some examples, the adult toy can be a common adult toy for use with a lubricant capsule containing cannabinoid extract lubricant.

The adult toy can include a proximal portion configured to interact with testicles of the user and a distal portion configured to be inserted into an anus of the user during use of the adult toy. The proximal portion and the distal portion can be so oriented with respect to each other, thereby defining a shape of the adult toy, that the distal portion is configured to stimulate a prostate of the user while the proximal portion stimulates the testicles of the user.

The adult toy can further include lubricant delivery mechanism configured to deliver said cannabinoid extract lubricant from the lubricant capsule to the user. The lubricant delivery mechanism can further include: a lubricant extraction mechanism configured to be in fluid communication with the lubricant capsule and extract the cannabinoid extract lubricant therefrom; a first conduit extending from the lubricant extraction mechanism and configured to deliver the cannabinoid extract lubricant therethrough; a first lubricant outlet port positioned at a distal end of the distal portion and in fluid communication with the first conduit for delivering the cannabinoid extract lubricant inside the anus of the user. The lubricant delivery mechanism can further include: a second conduit extending from the lubricant extraction mechanism and configured to deliver the cannabinoid extract lubricant therethrough; a second lubricant outlet port positioned at a proximal end of the distal portion and in fluid communication with the first conduit for delivering the cannabinoid extract lubricant at an entrance of the anus of the user.

The lubricant extraction mechanism can include a pumping mechanism configured to pump the cannabinoid extract lubricant from the lubricant capsule through at least one of the first and the second conduits.

The adult toy can further include a first vibrator motor configured to move the distal portion, and a second vibrator motor configured to move the proximal portion. In some examples, the first and the second vibrator motors can constitute parts of a single vibration unit. The adult toy can further include a heating mechanism configured to heat the cannabinoid extract lubricant prior to its delivery to the user.

The cannabinoid extract lubricant includes at least one of CBD oil and THC oil.

According to a seventh aspect of the presently disclosed subject matter there is provided a capsule containing a cannabinoid extract lubricant, configured for use with the adult toy according to any one of above-described aspects. The cannabinoid extract lubricant can include at least one of CBD oil and THC oil.

According to an eighth seventh aspect of the presently disclosed subject matter there is provided a kit including: an adult toy according to any one of the first, third, fourth, or fifth aspect; and an operative head according to the second aspect.

According to a ninth aspect of the presently disclosed subject matter there is provided a condom including: a main condom portion; and at least one pocket located at a distal condom portion of the condom, the at least one pocket being configured to hold a lubricant and to selectively dispense the lubricant during use of the condom. The at least one pocket can include a material being at least partially permeable, disposable, tear able, or pierceable. The at least one pocket can include a material configured to dissolve during use thereby releasing the lubricant.

In some examples, the at least one pocket can be an external pocket located at an external surface of the condom and is configured to dispense the lubricant into a vagina of a user during the use of the condom. In some examples, the at least one pocket can be an internal pocket located at an internal surface of the condom and is configured to dispense the lubricant within the condom during the use of the condom. In some examples, the at least one pocket can include two pockets including an external pocket located at an external surface of the condom and configured to dispense the lubricant into a vagina of a user during the use of the condom, and an internal pocket located at an internal surface of the condom and is configured to dispense the lubricant within the condom during the use of the condom.

BRIEF DESCRIPTION OF THE DRAWINGS

In order to understand the presently disclosed subject matter and to see how it can be carried out in practice, embodiments will be described, by way of non-limiting examples, with reference to the accompanying drawings, in which.

DETAILED DESCRIPTION

Figure 1A:
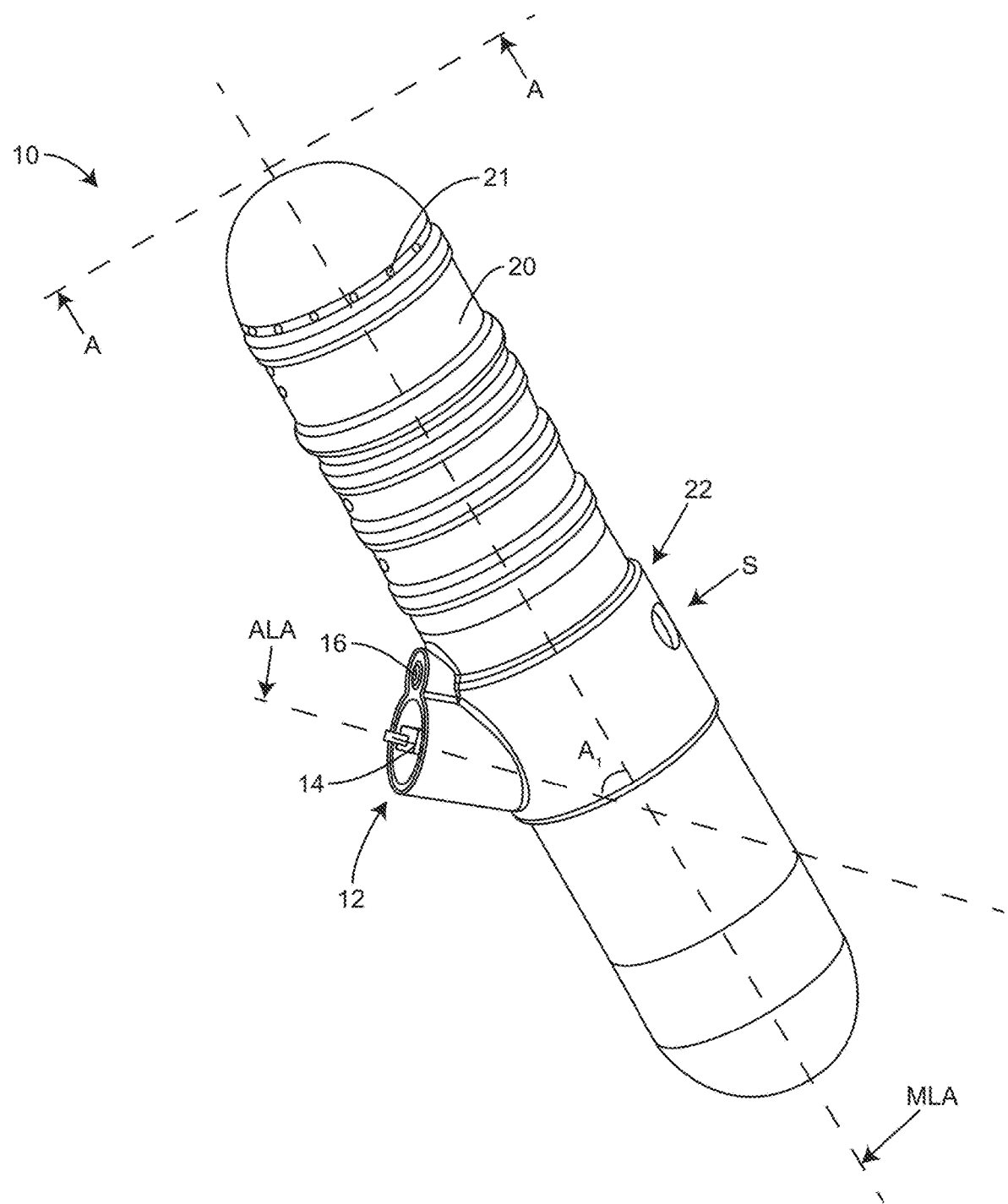
FIG. 1A is a perspective view of an adult toy according to an example of the presently disclosed subject matter.
Figure 1B:
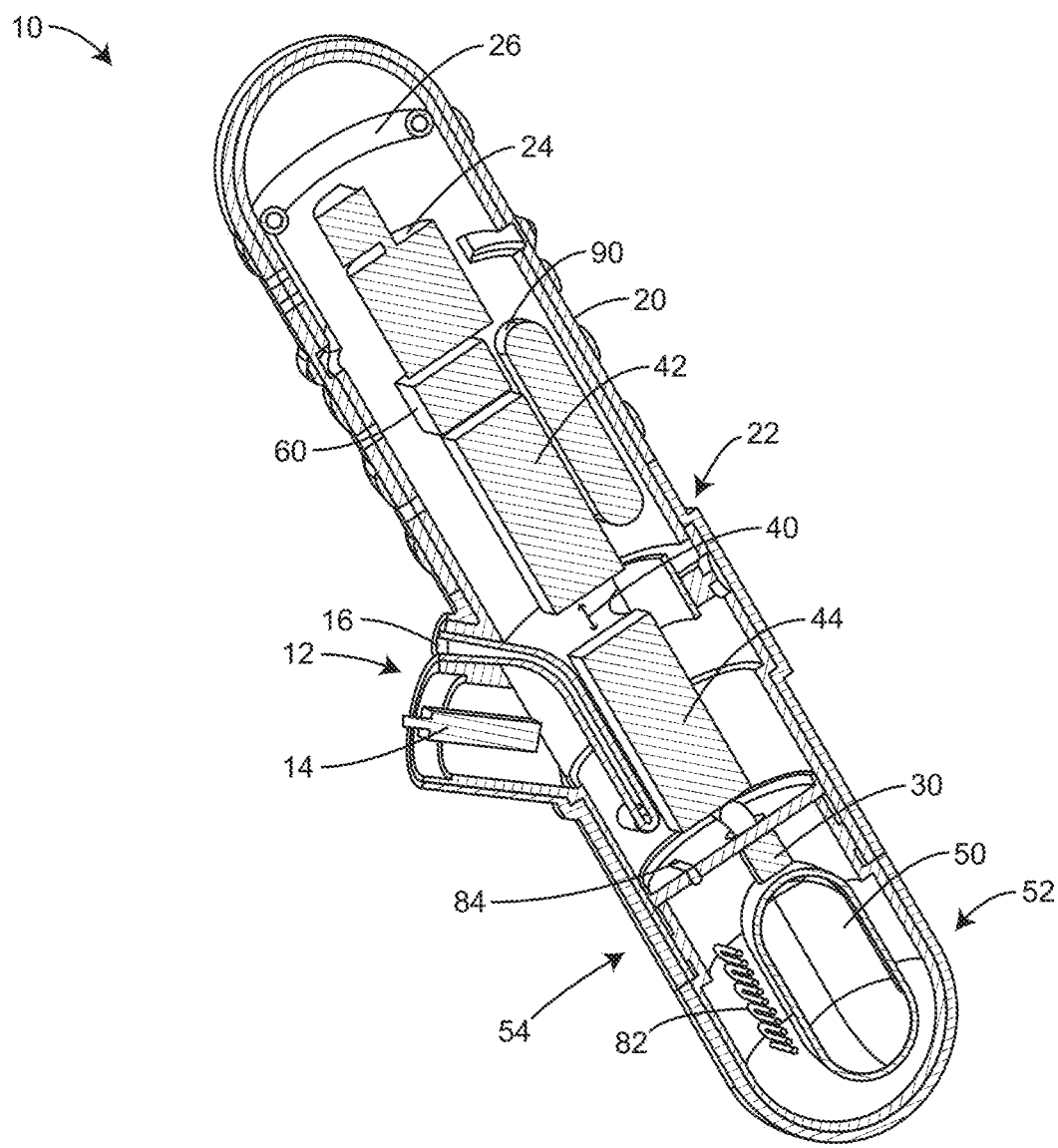
FIG. 1B is a cross-sectional view taken along line A-A in FIG. 1A.

The following detailed description sets forth general and specific details about features of the adult toy according to various examples of the presently disclosed subject matter. It is to be understood herein that all the features detailed below are not essential for realization of other of the features. For instance, the adult toy can operate with some selective features out of the features detailed below, and in some specific examples, the adult toy can have all the features detailed below.

The adult toys described below can provide increased pleasure to a user thereof. In addition to the sexual pleasure, the adult toys disclosed herein provide medicinal relief from sexual and mental problems including problems with ability to have an intercourse such as: anxiety and physical pain. The adult toys disclosed herein deliver (dispense) a lubricant, such a sexually stimulating substance at the sexual organs of the user. The lubricant is a cannabinoid extract, and more particularly CBD and/or THC oil. The euphoric high associated with THC helps to slow things down, and to intensify feelings of sexual pleasure. The CBD oil is known to reduced discomfort, enhance sensations, reduce pain, and ease stress and anxiety. For example, different researches suggest that CBD is able to lower inflammation by affecting the body's activity with endocannabinoid receptors. This includes both chronic and acute inflammation. The CBD oil can handle various medical conditions, such as: vulvodynia, veganism's, vaginal scarring, pelvic floor dysfunction, uterine fibroids, ovarian cysts, interstitial cystitis. The adult toys disclosed herein, in addition to providing sexual stimulation at the sex organs, provide these lubricants at the sex organs to enhance the pleasure and/or relief for which the adult toy is being used by the user. In addition, the adult toys have mechanisms to heat the lubricants prior to its delivery for further enhancing the pleasure and/or relief.

Reference is now made to FIGS. 1A to 1H illustrating an adult toy 10 according to an example of the presently disclosed subject matter. The adult toy 10 in general is a sex toy configured for use to stimulate sex organs of a user, and more particularly a vagina and clitoris of a female user. The adult toy 10 has a head port 12 configured for removably attaching thereto one or more operative heads, each operative head including at least one operational unit, described in detail herein further below with respect to FIGS. 2A to 5E. The adult toy 10 further has a motor 14 positioned at the head port 12 and configured to be operationally coupled to the operational unit of each of the operative heads for facilitating performance of operation thereof.

In general, the head port 12 is configured for removably attaching thereto the operative heads by an attaching action. The attaching action can be simply pressing the operative head on to the head port 12 along a longitudinal axis thereof. The motor 14 is configured to be operationally coupled to the corresponding operational units during said attaching action. In the illustrated example, the head port 12 extends along its longitudinal axis ALA and is configured to receive the operative heads therealong. The operative head can be pressed on to the head port 12 along the longitudinal axis ALA and attached thereto by for example, a snap attachment. In some examples, the attachment can be by a bayonet twist lock or by a simple frictional attachment by virtue of dimensions of the head port and the operative heads. The motor 14 is configured, i.e., structured, positioned, and oriented so as to be operationally coupled to the operational unit of the operative head when the operative head is pressed on to the head port 12 for attaching thereto.

The head port 12 further includes a lubricant delivery port 16 configured for delivering a lubricant therethrough. The lubricant be a sexually stimulating substance whose composition is described later herein below. The lubricant delivery port 16 can be connected to a lubricant source to deliver the lubricant. The lubricant delivery port 16 is configured, i.e., structured, positioned, and oriented so as to connect to a lubricant port extension element of the operative head when the operative head is attached to the head port 12. The connection between the lubricant delivery port 16 and the lubricant port extension element is leak-proof connection for delivery of the lubricant therethrough. Moreover, this connection is established during attachment of the operative head to the head port 12, i.e., by the single attaching action. Thus, the single action of attaching the operative head to the head port causes the attachment of the operative head to the head port, operational coupling of the motor 14 with the operational unit of the operative head, and connection between the lubricant delivery port 16 and the lubricant port extension element of the operative head.

In the illustrated example, the adult toy 10 further includes a main head 20 attached to a main port 22. It is to be understood herein that although in the illustrated example, the main head 20 is fixedly attached to the main port 22, in other examples, the main port 22 can be configured for removably attaching thereto one or more main heads one by one. The replaceable main heads can have different shapes (curvatures), textures (dotted, striped, etc.), dimensions (for example, of insertable portion), and/or operational units. The main head 20 is configured for being inserted into a vagina (or anal cavity) of a user of the adult toy. The main head 20 is attached to the main port 22 along its longitudinal axis MLA, which also constitutes the main longitudinal axis of the adult toy 10. Although in the illustrate example, the main head 20 extends along the main longitudinal axis MLA of the adult toy 10, it is to be understood herein that in some examples the main head can extend at an angle with respect to the main longitudinal axis.

The main operational unit can be a vibrator unit and the adult toy 10 includes a main motor 24 configured to operate the vibrator unit. In other words, the main motor 24 is configured to move the main head in a predetermined pattern to cause stimulations at or inside the vagina when the adult toy is in use. The main operational unit can be any other of the operational units described further below with respect to FIGS. 2A to 5E and the main motor 24 can be configured to operate all or any of these operational units.

The adult toy further includes a main lubricant delivery port 26 configured for delivering therethrough a lubricant (same as or different from the lubricant delivered by the lubricant delivery port 16) to the vagina of the user. The main head 20 includes holes 21 corresponding the main lubricant delivery port 26 so that the lubricant can be delivered through the main head into the vagina when the adult toy 10 is in use.

Although in all the examples of the adult toy 10 described herein, the adult toy 10 includes the head port 12 as well as main head port 22, it is to be understood that the adult toy 10 can have only one head port, i.e., head port 12 that is configured for removably and selectively attaching thereto one or more operative heads for performing corresponding functions with the sexual organ of the user. All the components corresponding the main head 20, for example, the main port 22, the main motor 24, the main lubricant delivery port 26, are to be understood as not being essential, and the adult toy 10 can be realized without these components with only the head port 2 and its corresponding components.

As in the illustrated example, the adult toy 10 includes the main head 20 attached to the main head port 22, the head port 12 constitutes an auxiliary head port 12 and the operative heads (detailed herein below with reference to FIGS. 2A to 5E) and their operational units constitute auxiliary heads and auxiliary operational units. Similarly, the longitudinal axis of the auxiliary head port 12 constitute an auxiliary longitudinal axis ALA, the motor 14 and the lubricant delivery port 16 constitute respectively an auxiliary motor 14 and an auxiliary lubricant delivery port 16.

The auxiliary longitudinal axis ALA is inclined at an acute angle A1 with respect to the main longitudinal axis MLA when seen from the side of the main head port 22 and the auxiliary head port 12. The angle A1 is selected for the adult toy 10 to be used such the main head 20 can be inserted into the vagina of the user and the auxiliary heads, when attached to the auxiliary port 12, can interact with the clitoris of the user. In some examples, the connection between the auxiliary head port 12 and the main head port 22 can be made flexible enough to be adjusted by and according to the user while being rigid at least enough for the use of the adult toy 10. Thus, the adult toy 10 is configured to stimulate the vagina and the clitoris of the user simultaneously thereby significantly increasing the pleasure and/or relief whatsoever is the adult toy used for by the user. At the same time, the adult toy 10 is configured to deliver lubricant (same or different from both the ports) inside the vagina and at the clitoris simultaneously. The lubricant can be a sexually stimulating substance and/or can contain substances for medicinal use such as to address various sex related problems, as described in detail later herein below.

Figure 1C:
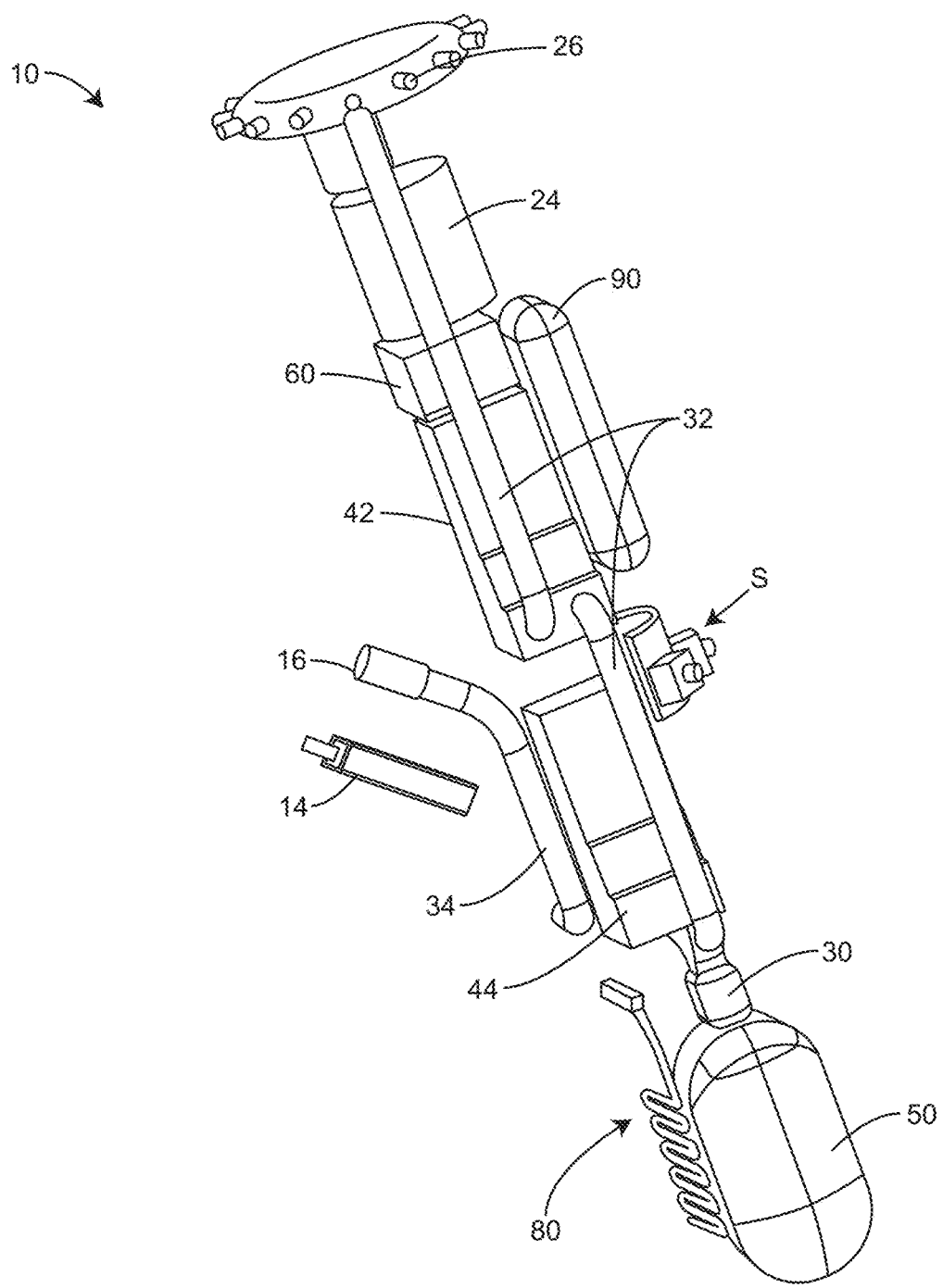
FIG. 1C is the same view as FIG. 1A with some of the components of the adult toy removed for illustration purposes.
Figure 1D:
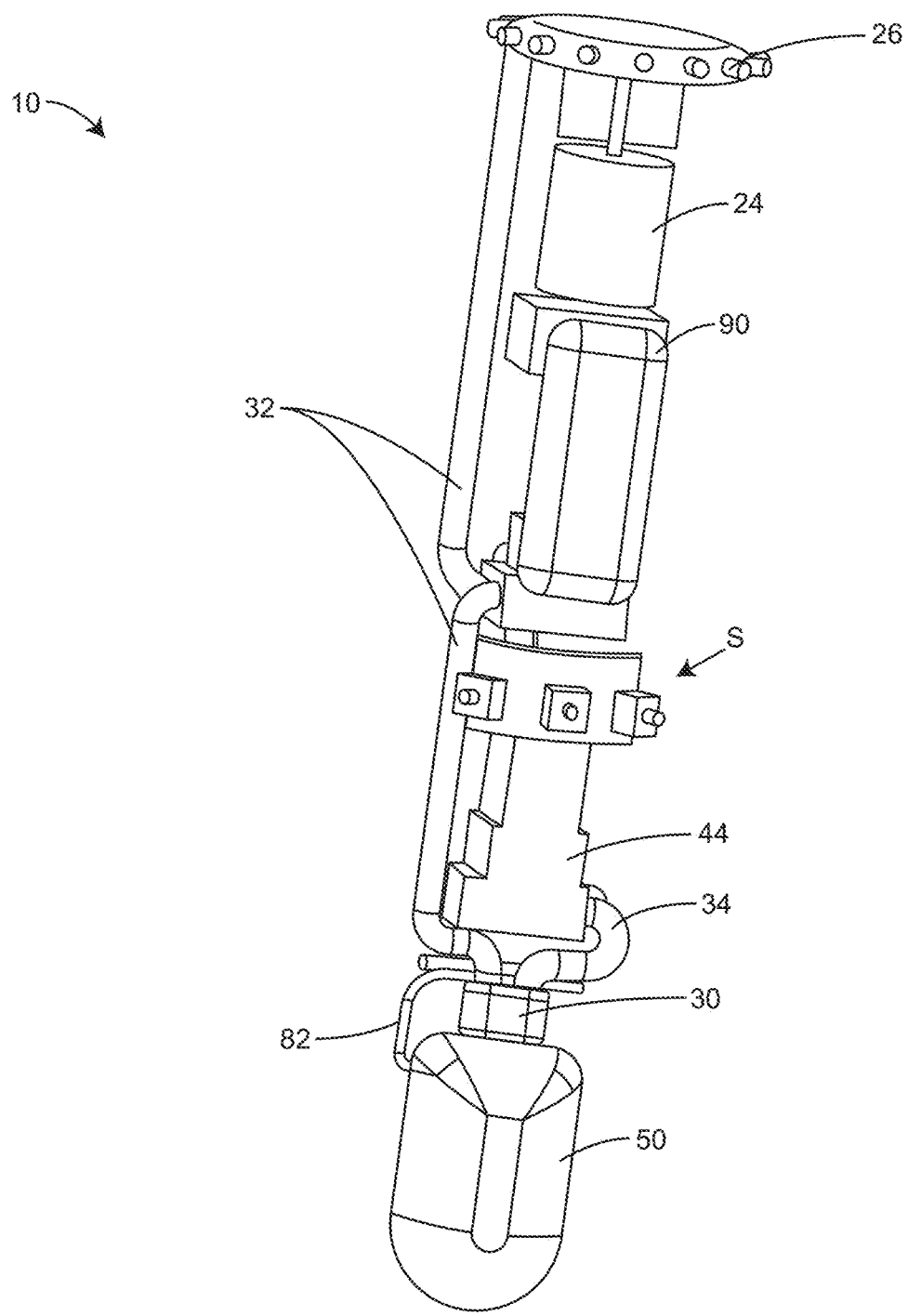
FIG. 1D is another perspective view of the adult toy as shown in FIG. 1C.
Figure 1E:
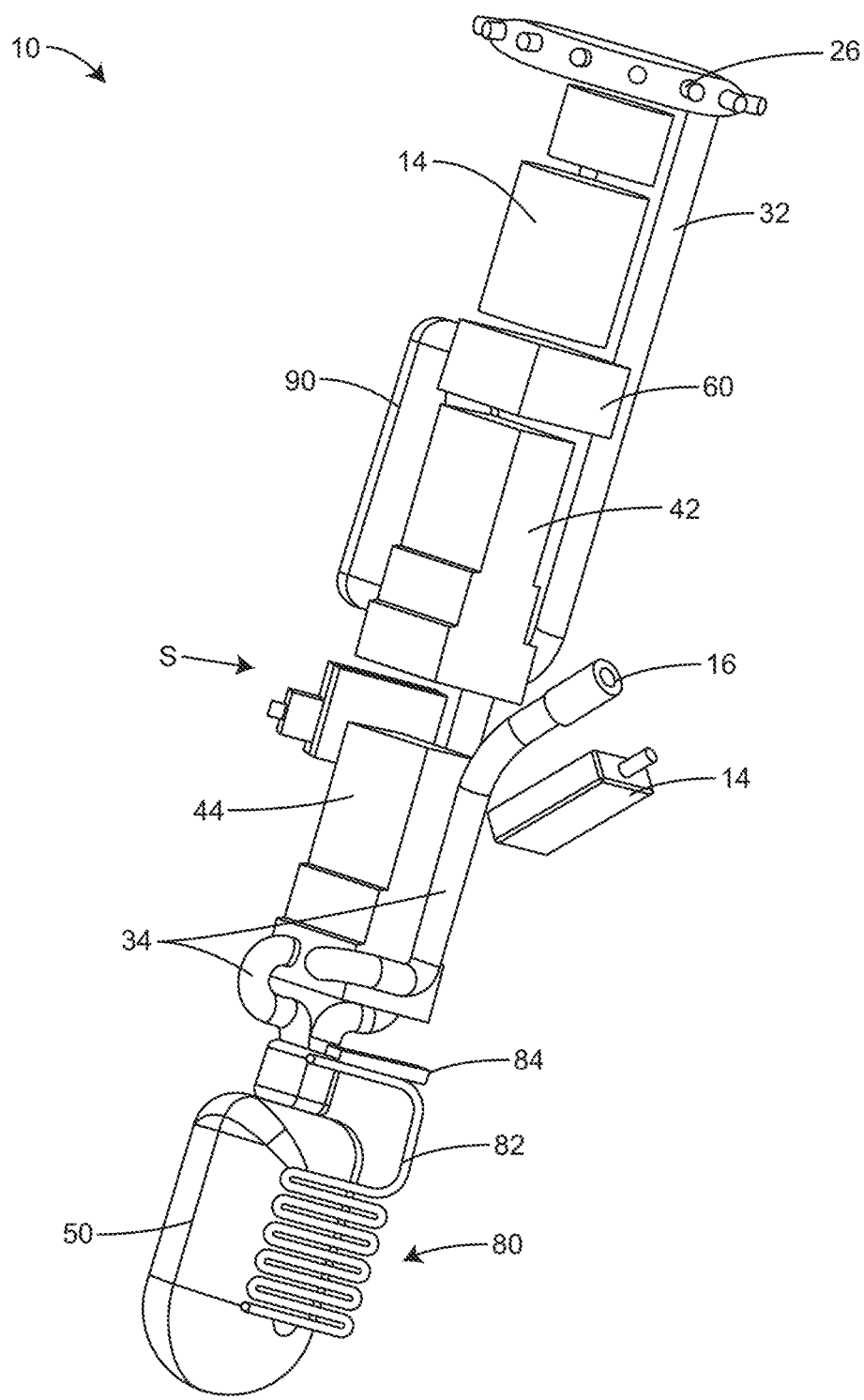
FIG. 1E is another perspective view of the adult toy as shown in FIGS. 1C and 1D.

As can be seen in FIGS. 1C to 1E, the adult toy 10 includes a lubricant inlet port 30 configured to be connected to a lubricant source containing a lubricant to be delivered through the adult toy 10. The adult toy 10 further includes a main conduit 32 configured to deliver said lubricant from the lubricant inlet port 30 through the main lubricant delivery port 26, and an auxiliary conduit 34 configured to deliver said lubricant from the lubricant inlet port through the auxiliary lubricant delivery port 16, which is distant from the main lubricant delivery port 26. The adult toy further includes a pumping mechanism 40 for pumping the lubricant from the lubricant inlet port 30 through each of the main conduit 32 and auxiliary conduit 34.

It is to be understood herein that although the adult toy 10 has been illustrated as having the features relating to the replaceability of operative heads as well as the lubricant being deliverable from two distant ports of the adult toy, the adult toy can be realized with any one set of these features. The adult toy 10 can be realized with only the features related to lubricant being deliverable from two distant ports of the adult toy without the adult toy necessarily having features related to replaceability of the operative heads, and vice versa. In other words, the presently disclosed subject matter includes within its scope an adult toy having the features related to the lubricant being deliverable from two distant ports of the adult toy with fixedly attached operative heads and the main head. For instance, the adult toy 10, according to some examples, can include fixed main head 20 and a fixed auxiliary head at the auxiliary head port 12, each having respective lubricant delivery ports configured for delivering the lubricant inside the vagina (through the main head) and at the clitoris (through the auxiliary head).

In the illustrated example, the main conduit 32 connects the lubricant inlet port 30 to the main lubricant delivery port 26, and the auxiliary conduit 34 connects the lubricant inlet port 30 to the auxiliary lubricant delivery port 16. The conduits 32 and 34 transfers the lubricant from the lubricant inlet port to the lubricant delivery ports for the delivery of the lubricant to the user therethrough. The lubricant inlet port is configured to be connected, to establish a fluid communication, to a lubricant source. The lubricant source can be any internal or external source containing the lubricant that is to be delivered to the sexual organ of the user. The lubricant can be a sexually stimulating substance and/or a medicinal drug to address sex related problems. In the illustrated example, the lubricant source is a replaceable lubricant capsule that can be received within the adult toy. However, in other examples, the lubricant source can be a refillable cartridge or an external single or multiple use lubricant source. In some examples, the lubricant source can include more than one lubricant sources, each containing different lubricants to be delivered to the vagina and the clitoris of the user. In such examples, the lubricant inlet port can be configured to be connected to the multiple lubricant sources and deliver one lubricant though the main conduit and another lubricant through the auxiliary conduit.

In the illustrated example, the lubricant source is a single lubricant source, i.e., the lubricant capsule 50. The lubricant inlet port 30 is a double one-way valve configured to be fluidly connected to the lubricant capsule 50 at one end and the main and the auxiliary conduits 32 and 34 on the other side. The pumping mechanism 40 includes a first peristaltic pump 42 associated with the main conduit 32 and configured to pump the lubricant from the lubricant source 50 and the lubricant inlet port 30 through the main conduit 32. The pumping mechanism 40 further includes a second peristaltic pump 44 associated with the auxiliary conduit 34 and configured to pump the lubricant from the lubricant source 50 and the lubricant inlet port 30 through the auxiliary conduit 34.

The main conduit 32 extends through the main head port 22 into the main head 20 and is in fluid communication with the main lubricant delivery port 26. The first peristaltic pump 42 is configured to deliver the lubricant through the main conduit 32 and the main lubricant delivery port 26 inside the vagina of the user via the main head 20 when the main head 20 is inserted in the vagina. The second peristaltic pump 44 is configured to, simultaneously or independently of the first peristaltic pump 42, deliver the lubricant through the auxiliary conduit 34 and the auxiliary lubricant delivery port 16 at the clitoris of the user via the auxiliary head when the auxiliary head is interacting with the clitoris. In order to deliver the lubricant to the clitoris, the auxiliary lubricant delivery port 16 is configured for being connected to the lubricant port extension element of the auxiliary head when the auxiliary head is attached to the auxiliary head port 12.

The adult toy 10 further includes a controller 60 configured for controlling the operations of the adult toy 10. The controller 60 is configured to control the pumping mechanism 40, i.e., the first peristaltic pump 42 and the second peristaltic pump 44. The controller can control the first and second peristaltic pumps either in coordination with each other or independently of each other. While operating the peristaltic pumps 42 and 44 in coordination with each other, the controller can control the operation of the peristaltic pumps 42 and 44 according to a predetermined pattern to suit the requirement of the user.

Further, the controller 60 is configured to control the operation of the auxiliary motor 14 and/or the main motor 24, either independently of or in coordination with each other according to a predetermined pattern. In some examples, the controller 60 can be configured to control the operations of the auxiliary motor 14, the main motor 24, the first peristaltic pump 42, and the second peristaltic pump 44 according to one or more predetermined pattern, each one to suit a particular requirement or preference for the sexual stimulation to be achieved by the adult toy. In some examples, the adult toy 10 can include different controllers (separate or forming a part of a single control system) for controlling the operations of the different components.

Figure 1F:
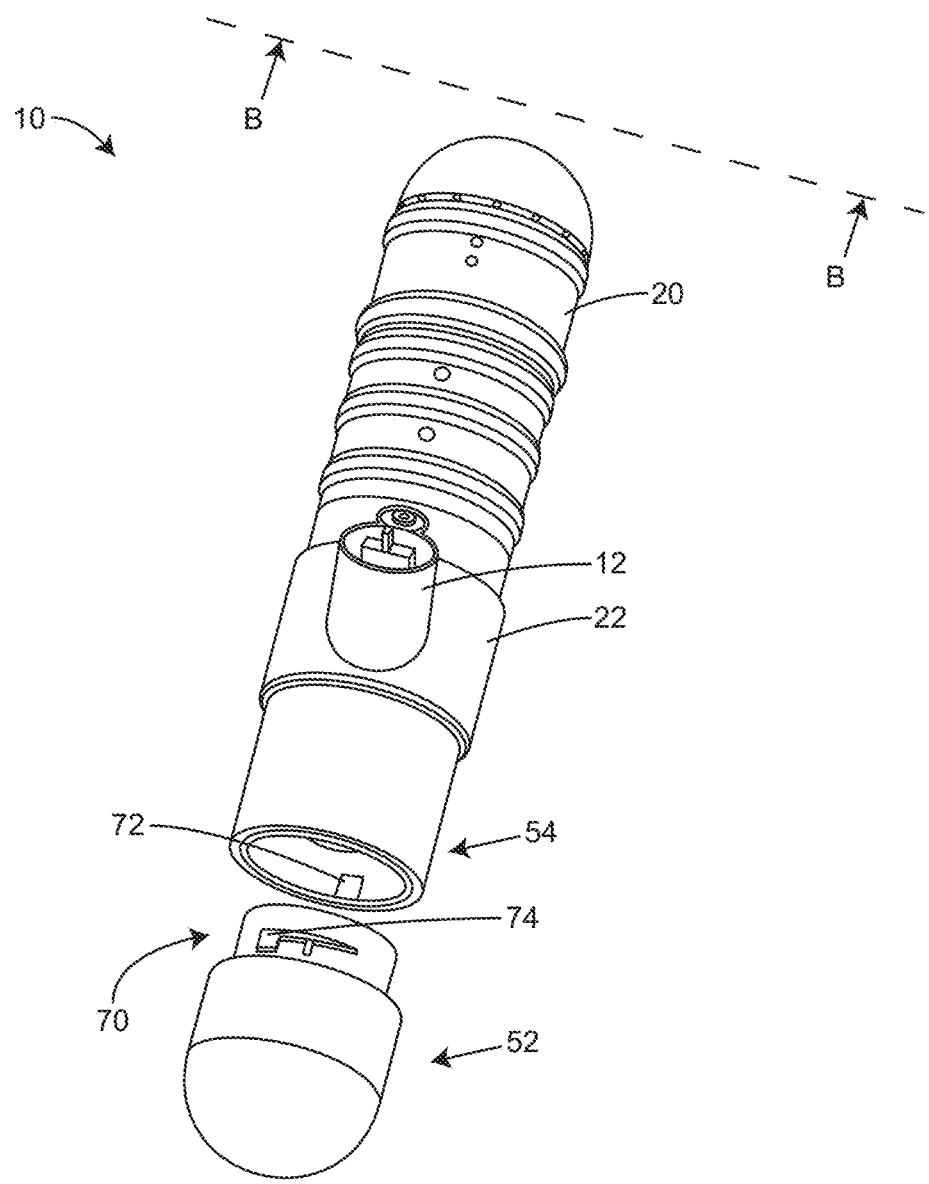
FIG. 1F is another perspective view of the adult toy as shown in FIG. 1A.
Figure 1G:
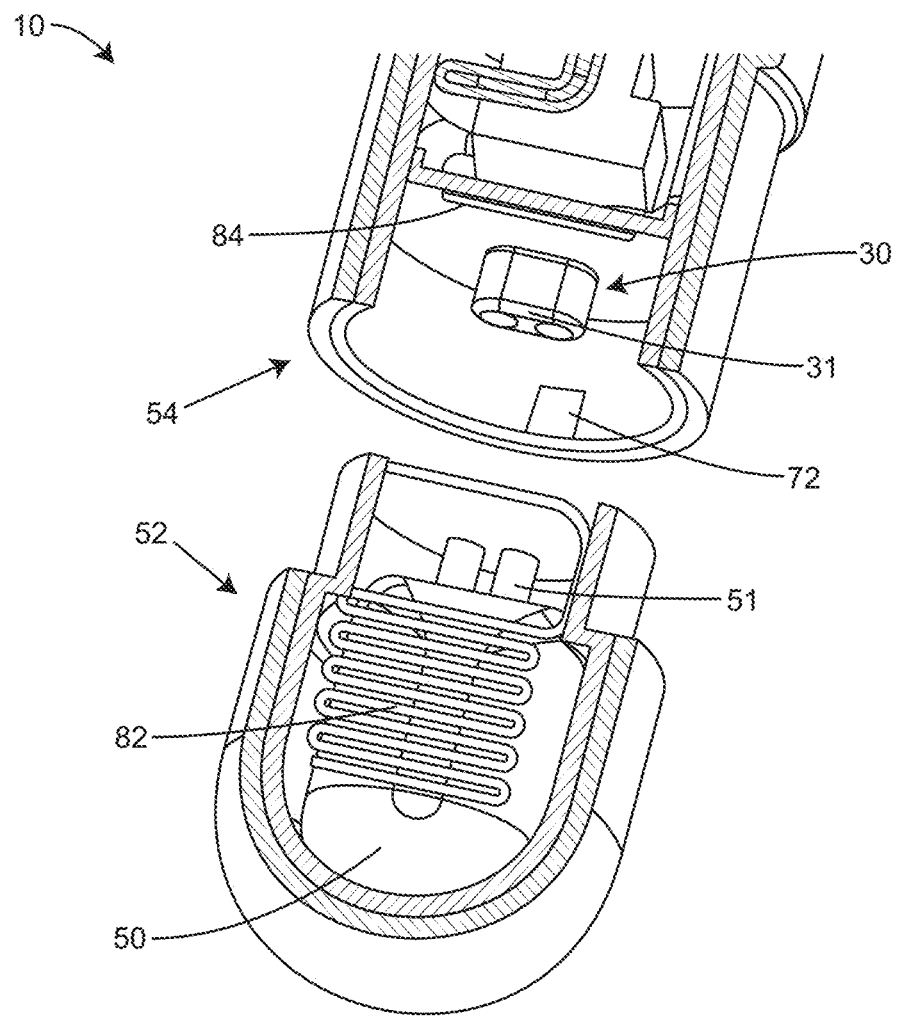
FIG. 1G is an enlarged view of a cross-section taken along line B-B in FIG. 1F.
Figure 1H:
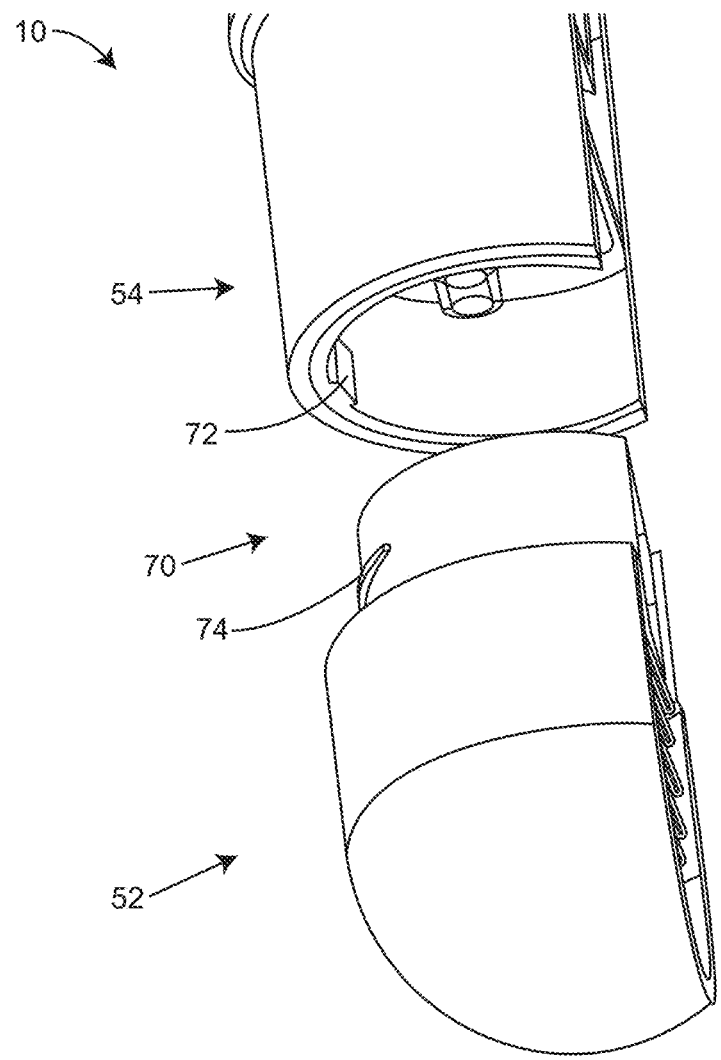
FIG. 1H is another view of the adult toy as shown in FIG. 1G.
Figure 2A:
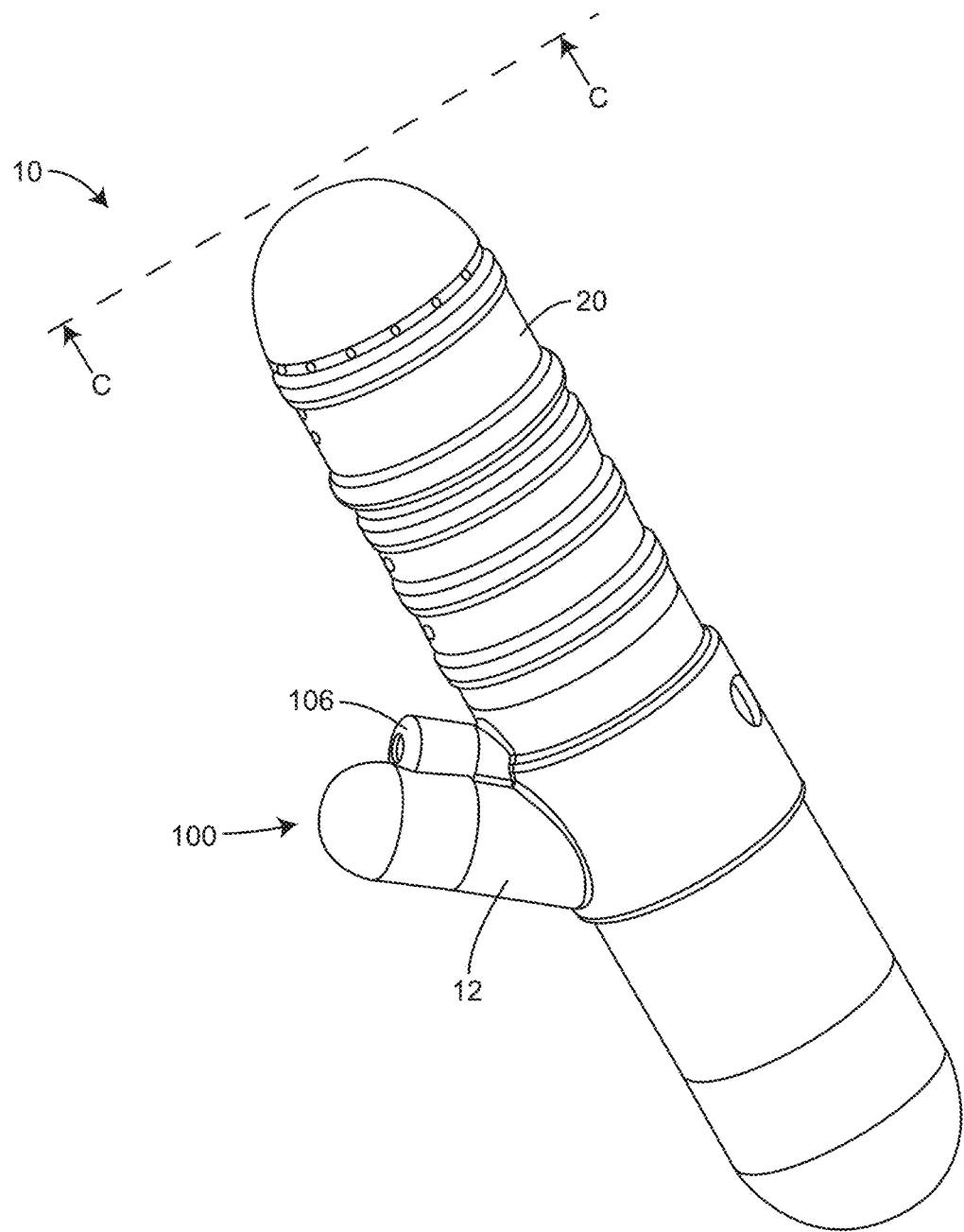
FIG. 2A is a perspective view of the adult toy of FIG. 1A with an operative head connected thereto according to an example of the presently disclosed subject matter.
Figure 2B:
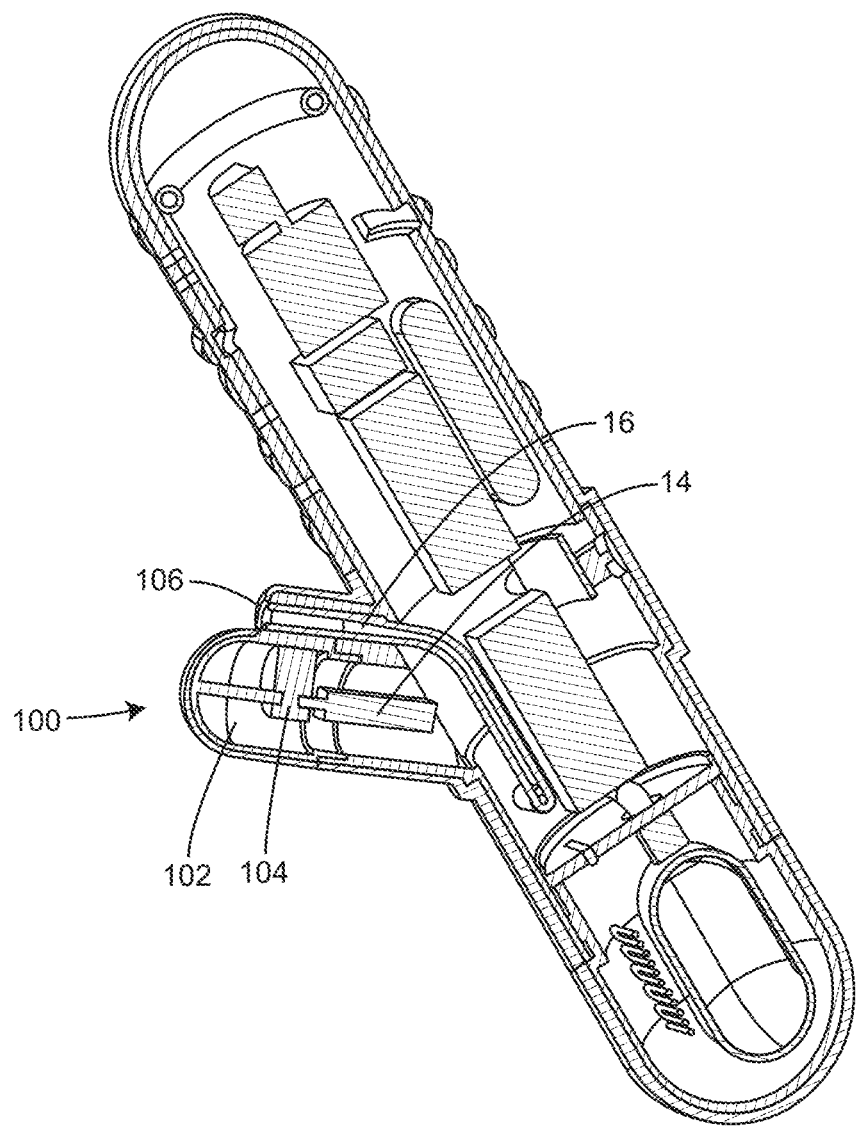
FIG. 2B is a cross-sectional view taken along line C-C in FIG. 2A.
Figure 2C:
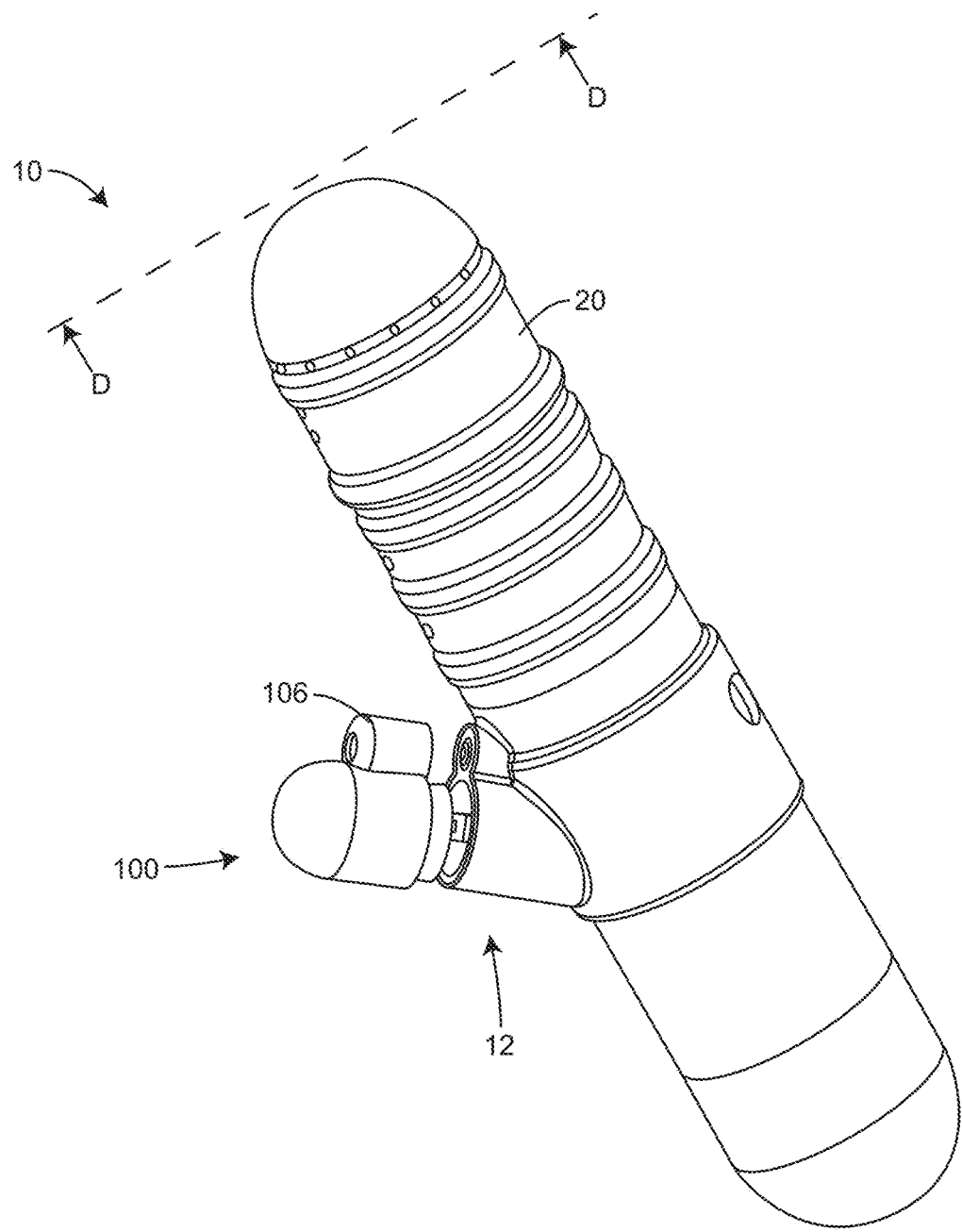
FIG. 2C is a partially exploded view of the adult toy of FIG. 2A.
Figure 2D:
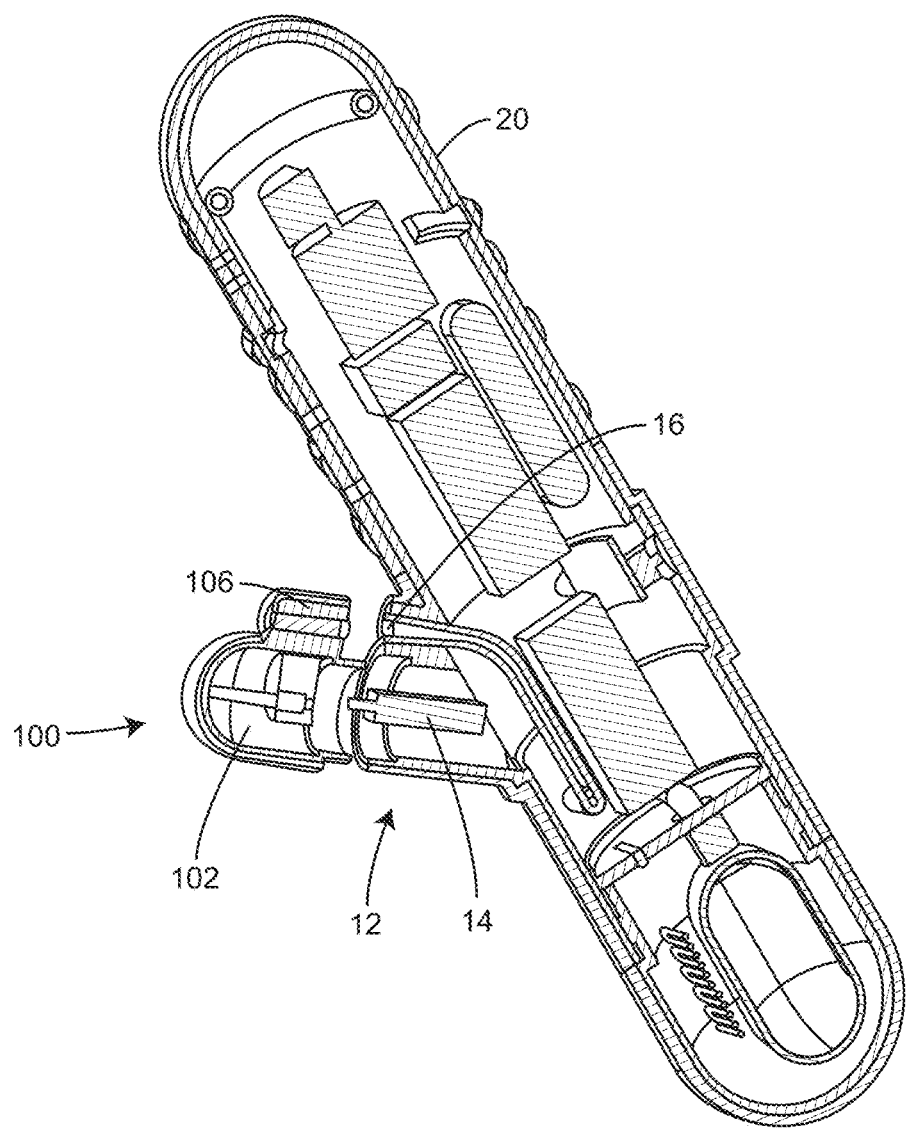
FIG. 2D is a cross-sectional view taken along line D-D in FIG. 2C.
Figure 3A:
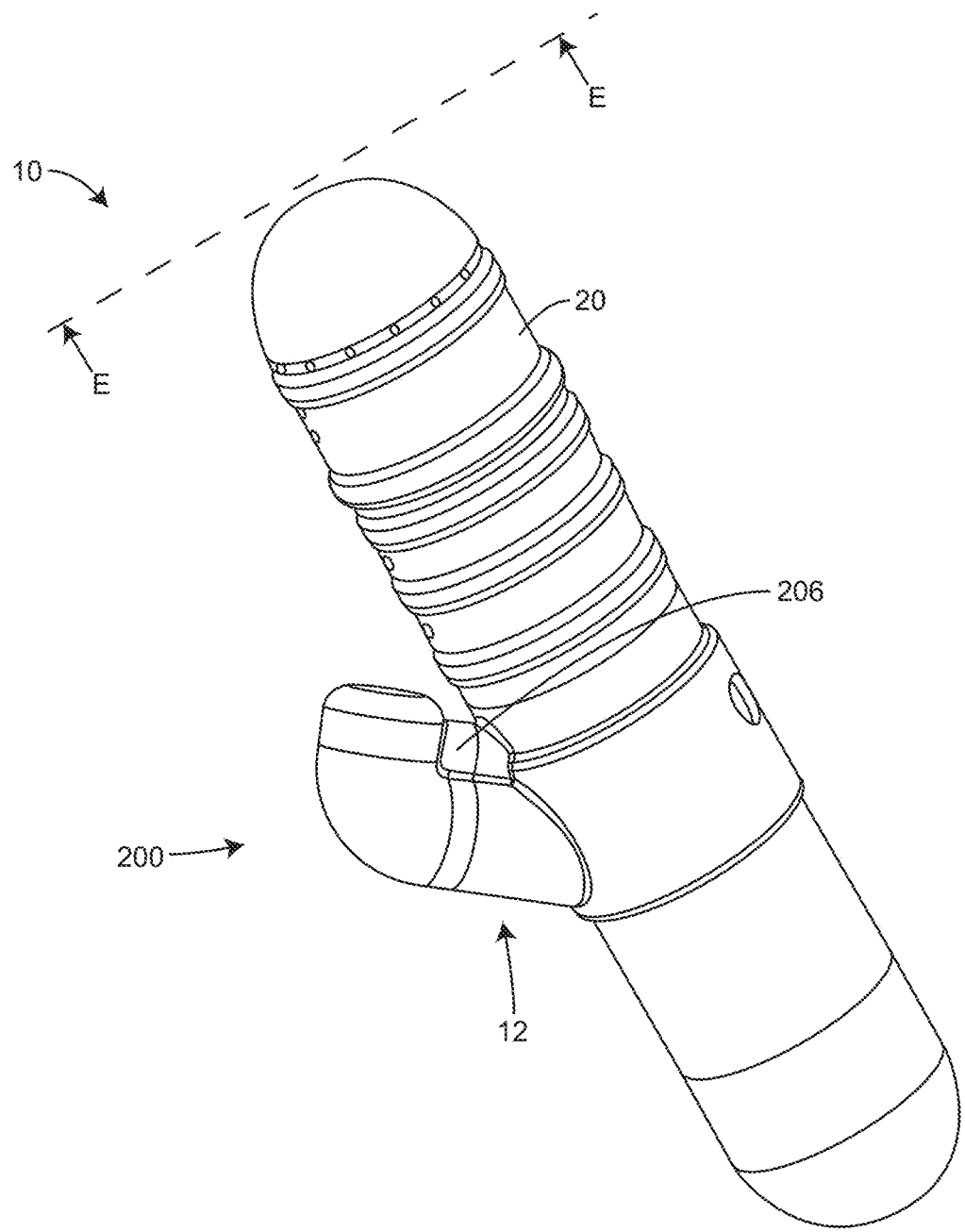
FIG. 3A is a perspective view of the adult toy of FIG. 1A with another operative head connected thereto according to another example of the presently disclosed subject matter.
Figure 3B:
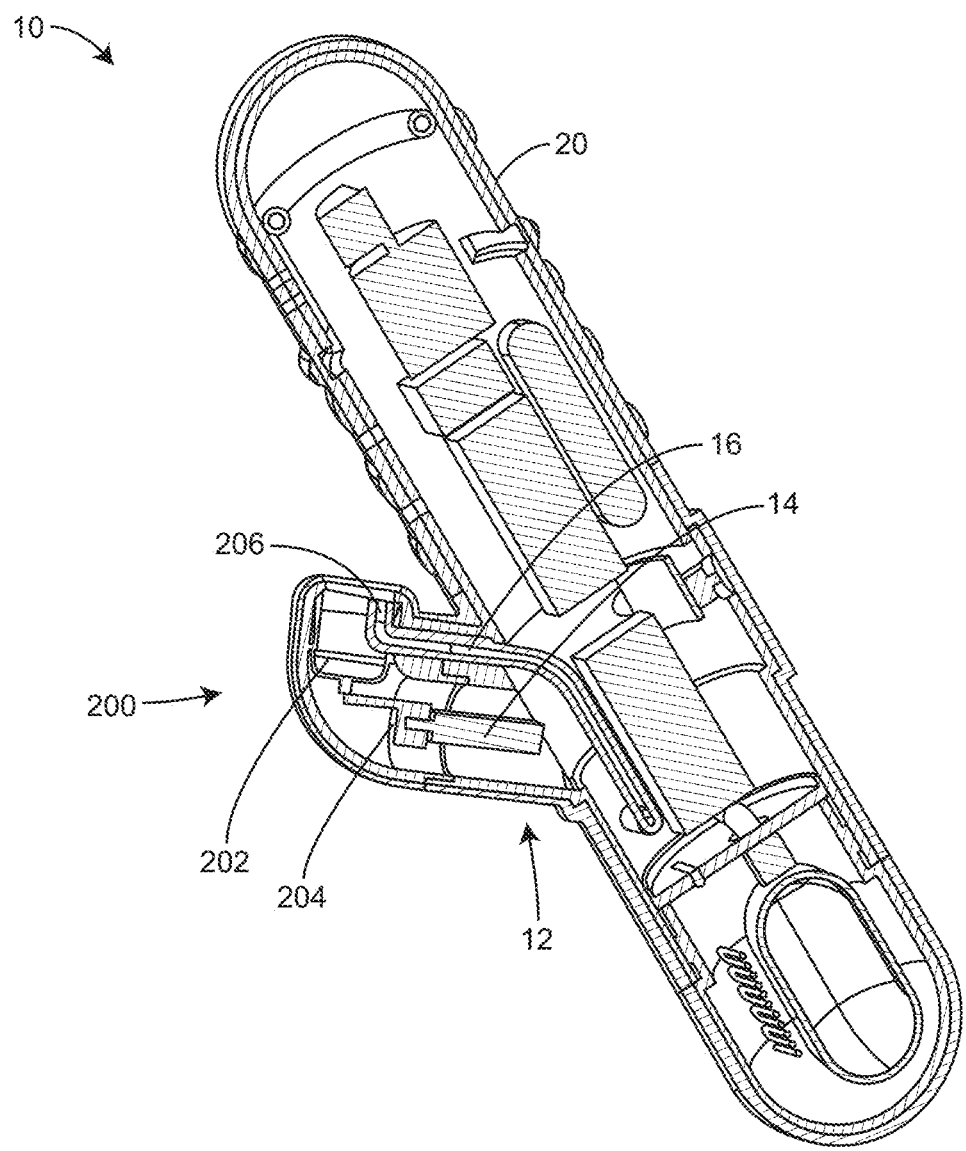
FIG. 3B is a cross-sectional view taken along line E-E in FIG. 3A.
Figure 3C:
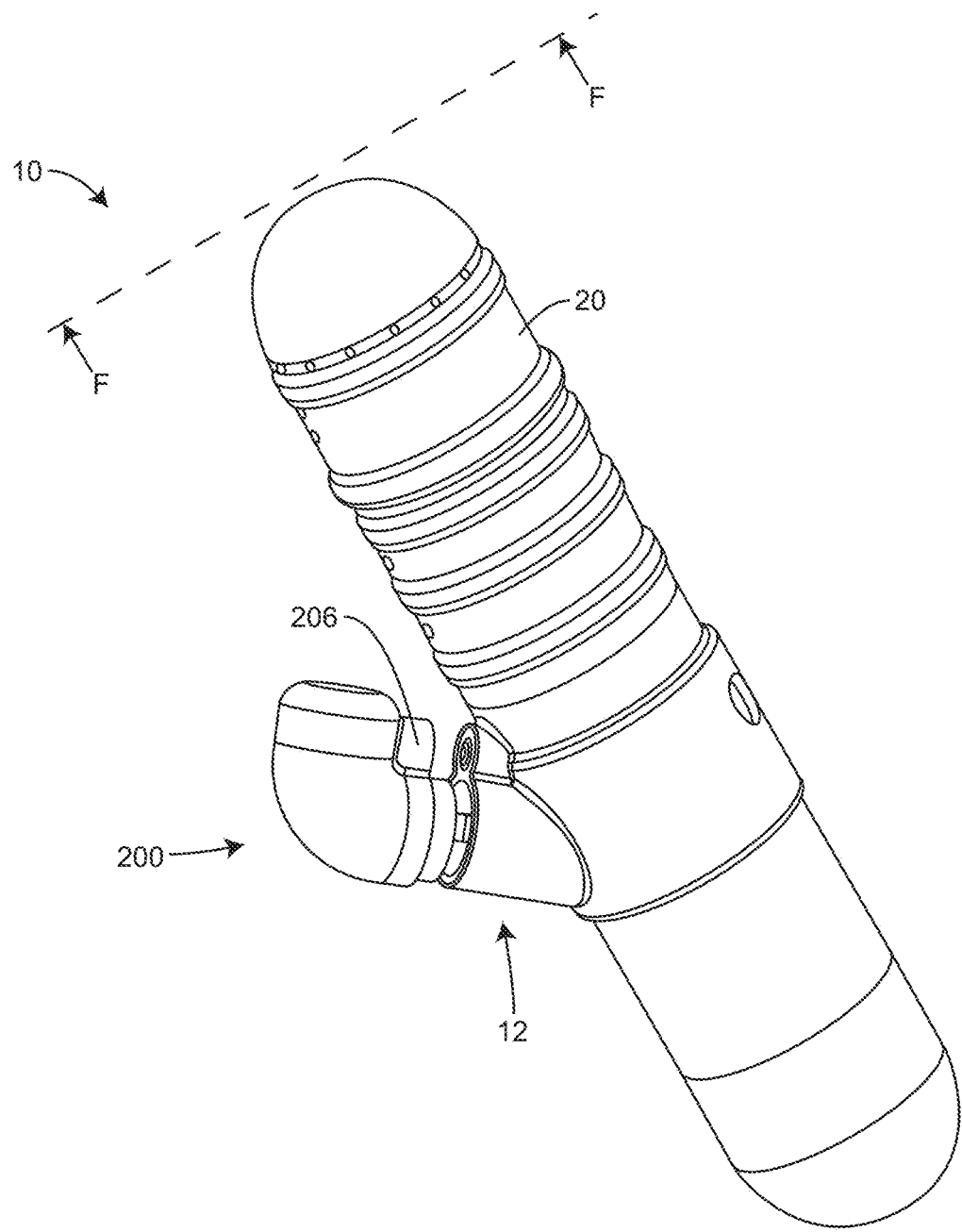
FIG. 3C is a partially exploded view of the adult toy of FIG. 3A.
Figure 3D:
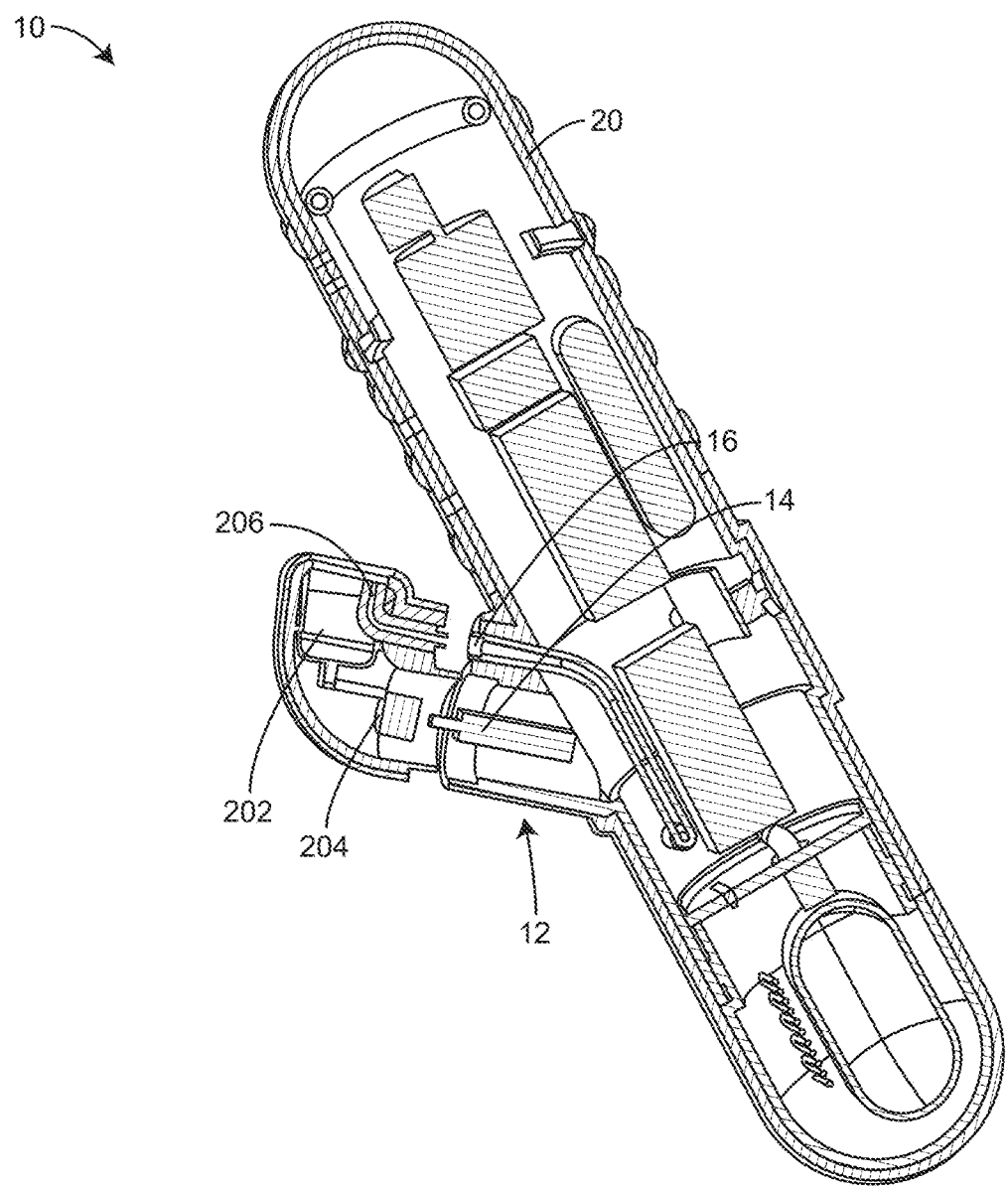
FIG. 3D is a cross-sectional view taken along line F-F in FIG. 3C.
Figure 4A:
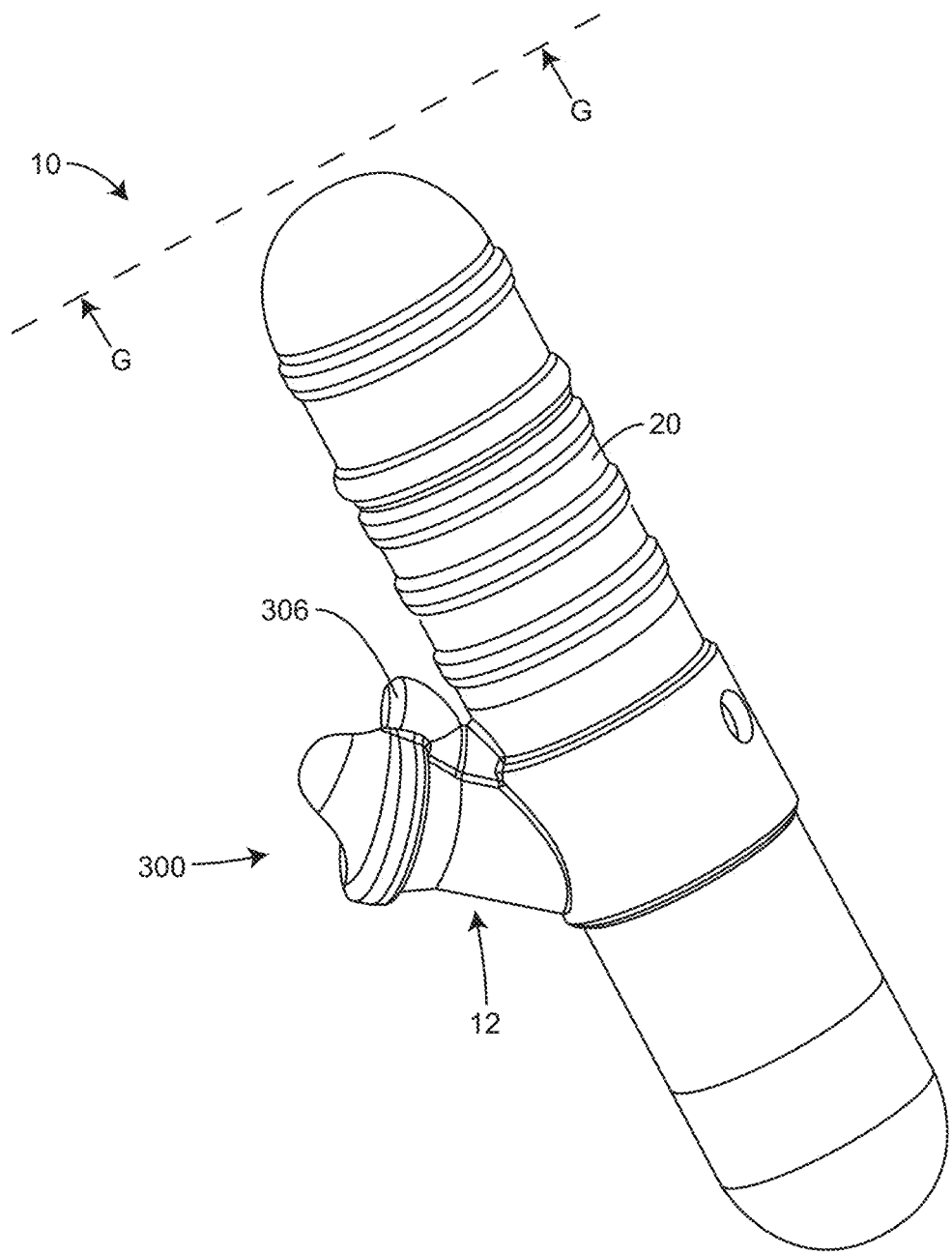
FIG. 4A is a perspective view of the adult toy of FIG. 1A with yet another operative head connected thereto according to yet another example of the presently disclosed subject matter.
Figure 4B:
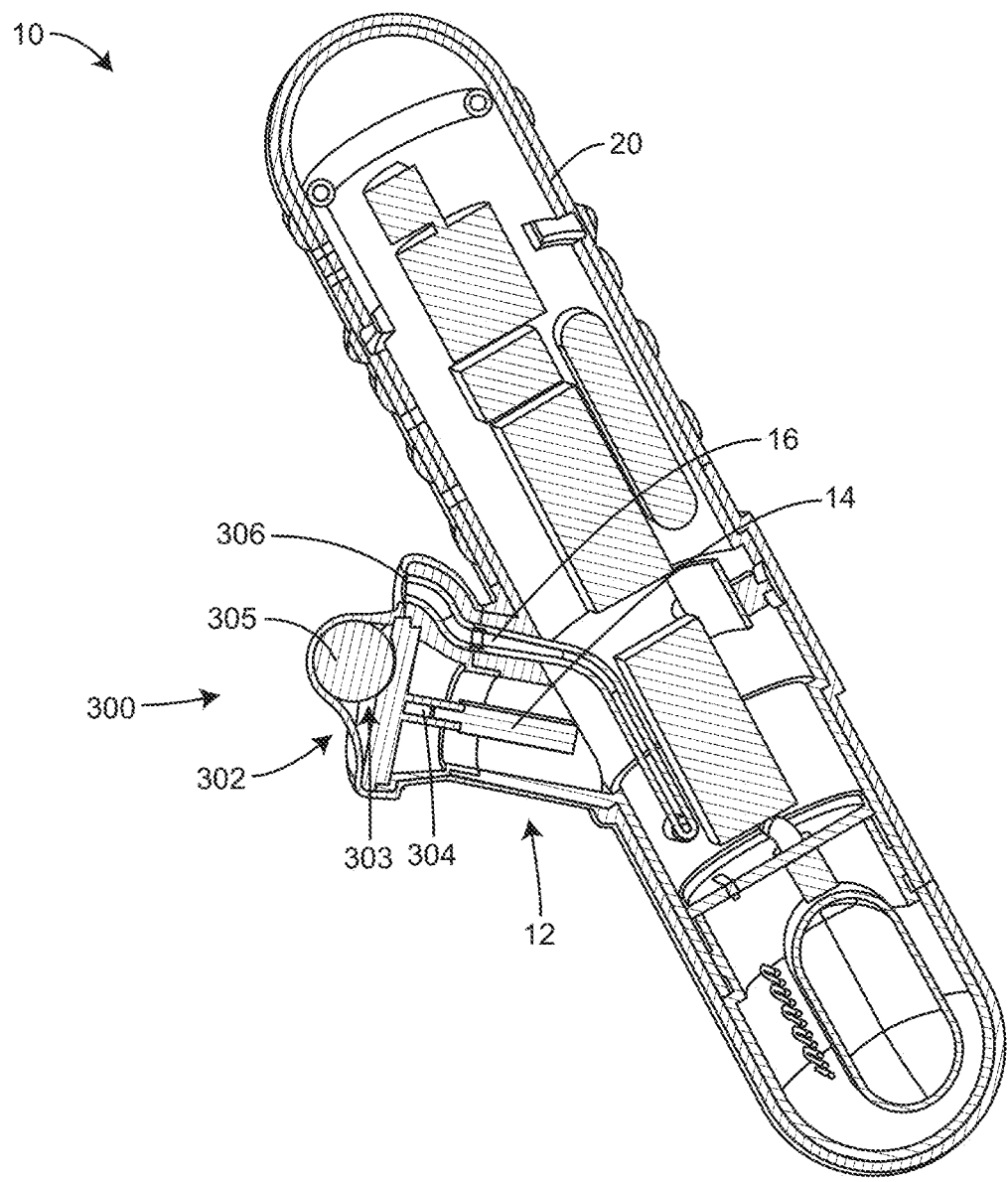
FIG. 4B is a cross-sectional view taken along line G-G in FIG. 4A.
Figure 4C:
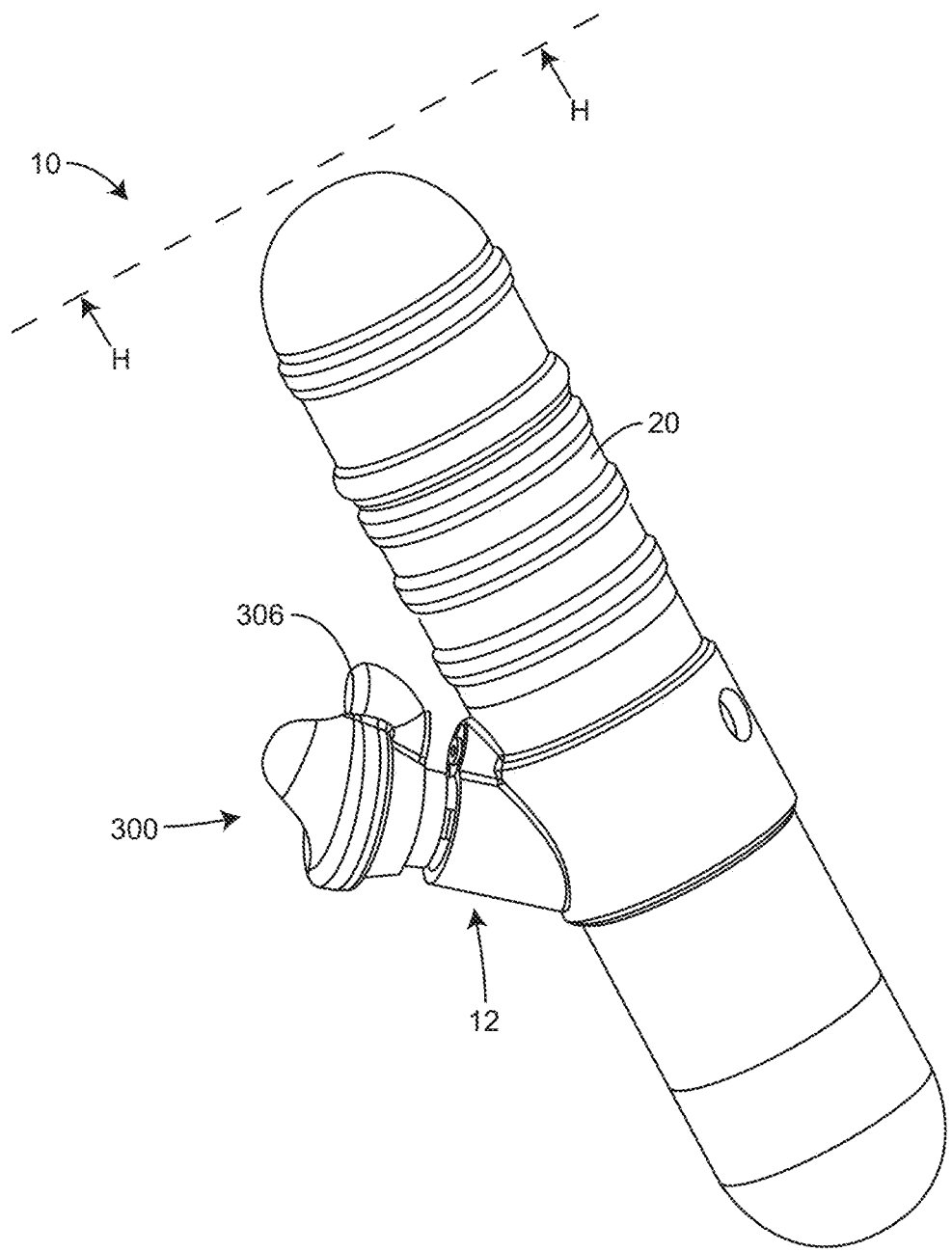
FIG. 4C is a partially exploded view of the adult toy of FIG. 4A.
Figure 4D:
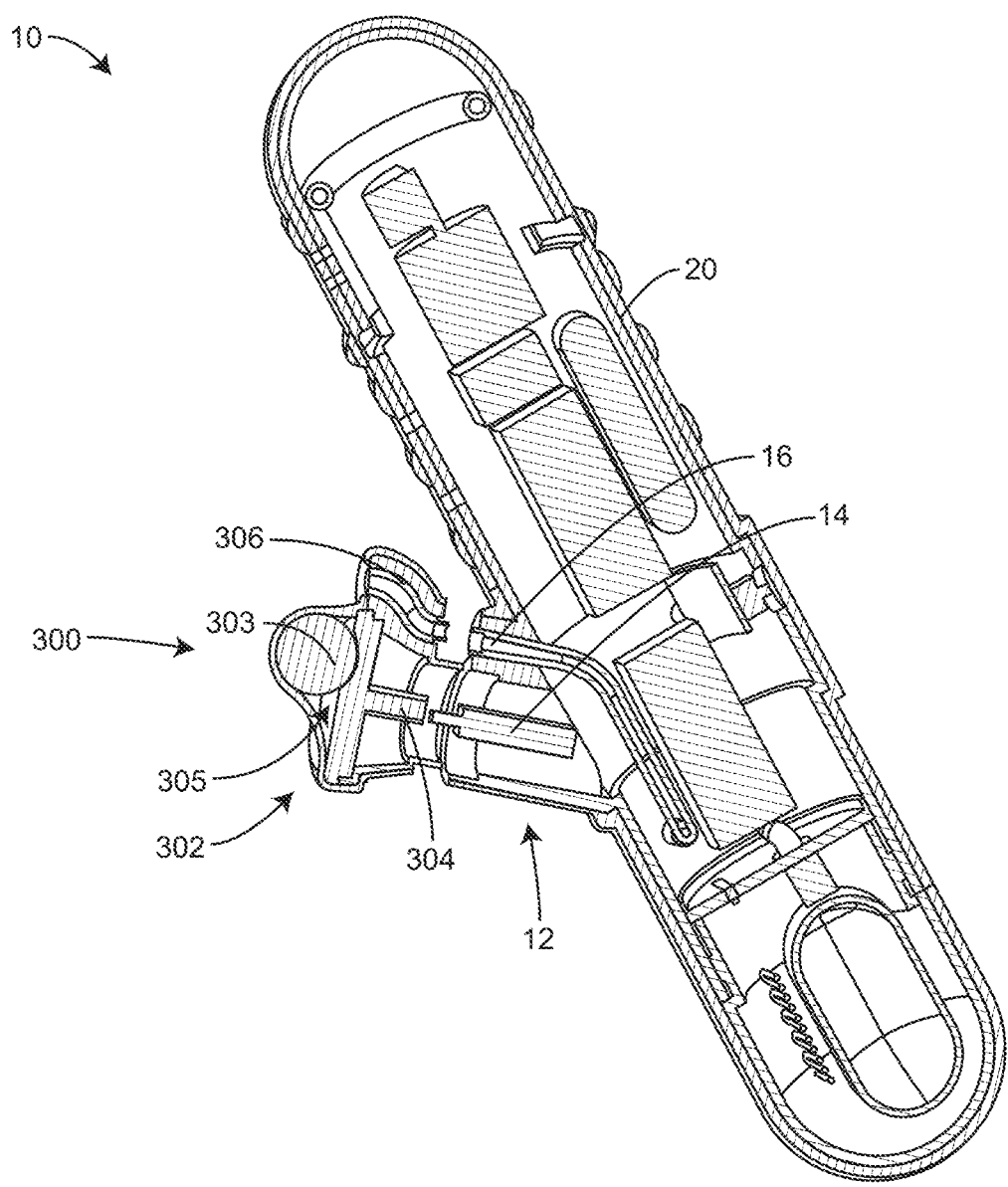
FIG. 4D is a cross-sectional view taken along line H-H in FIG. 4C.
Figure 5A:
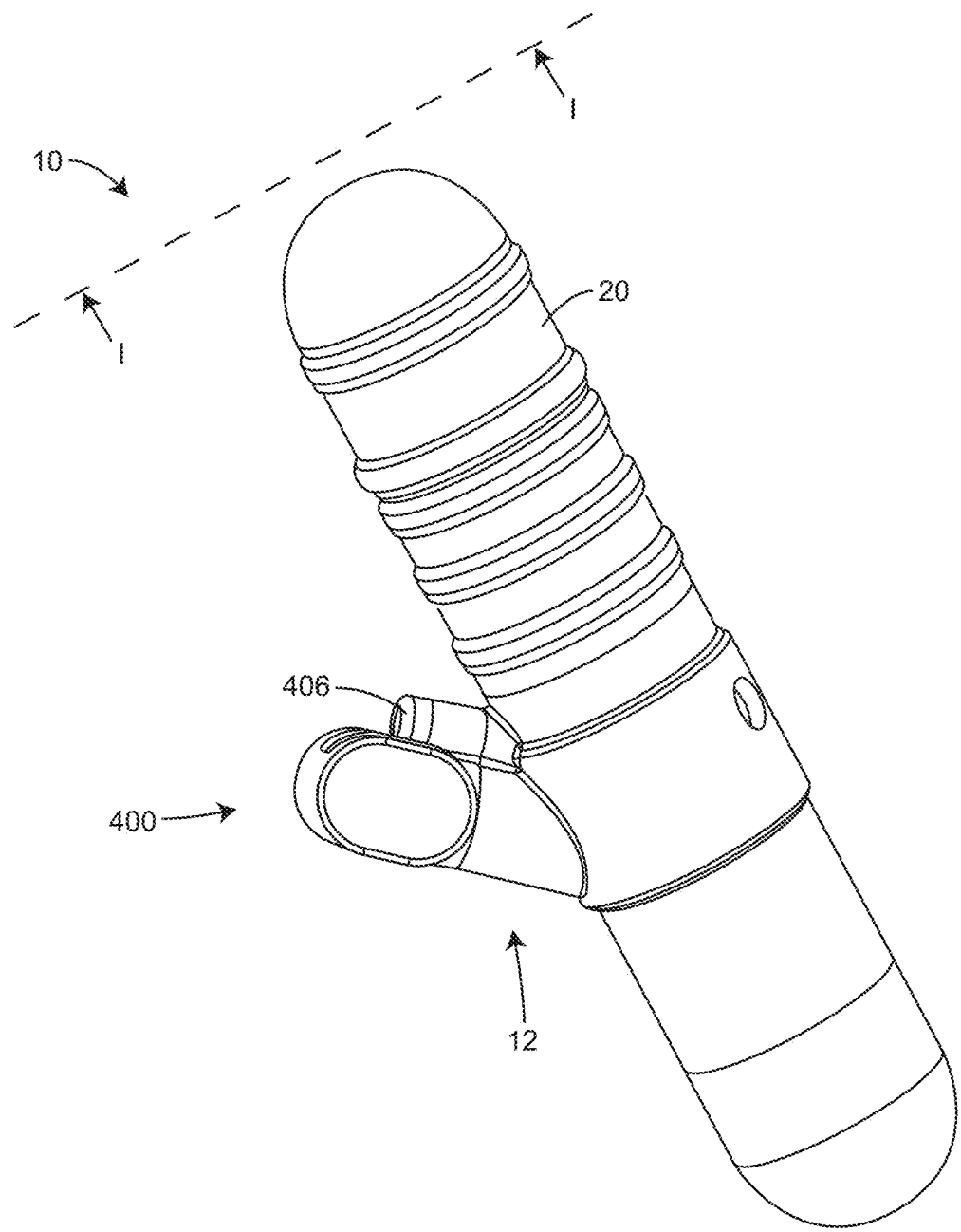
FIG. 5A is a perspective view of the adult toy of FIG. 1A with yet another operative head connected thereto according to yet another example of the presently disclosed subject matter.
Figure 5B:
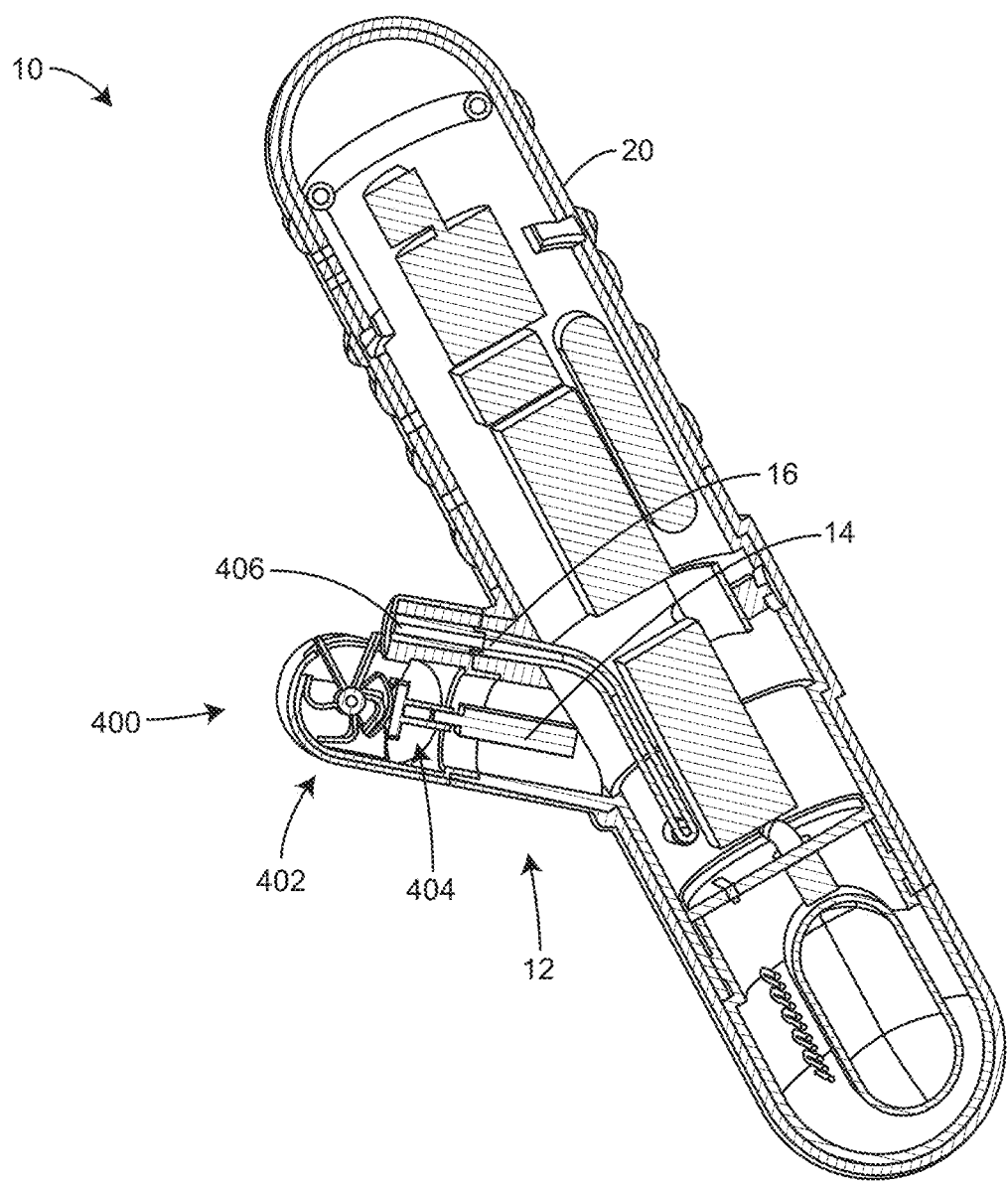
FIG. 5B is a cross-sectional view taken along line I-I in FIG. 5A.
Figure 5C:
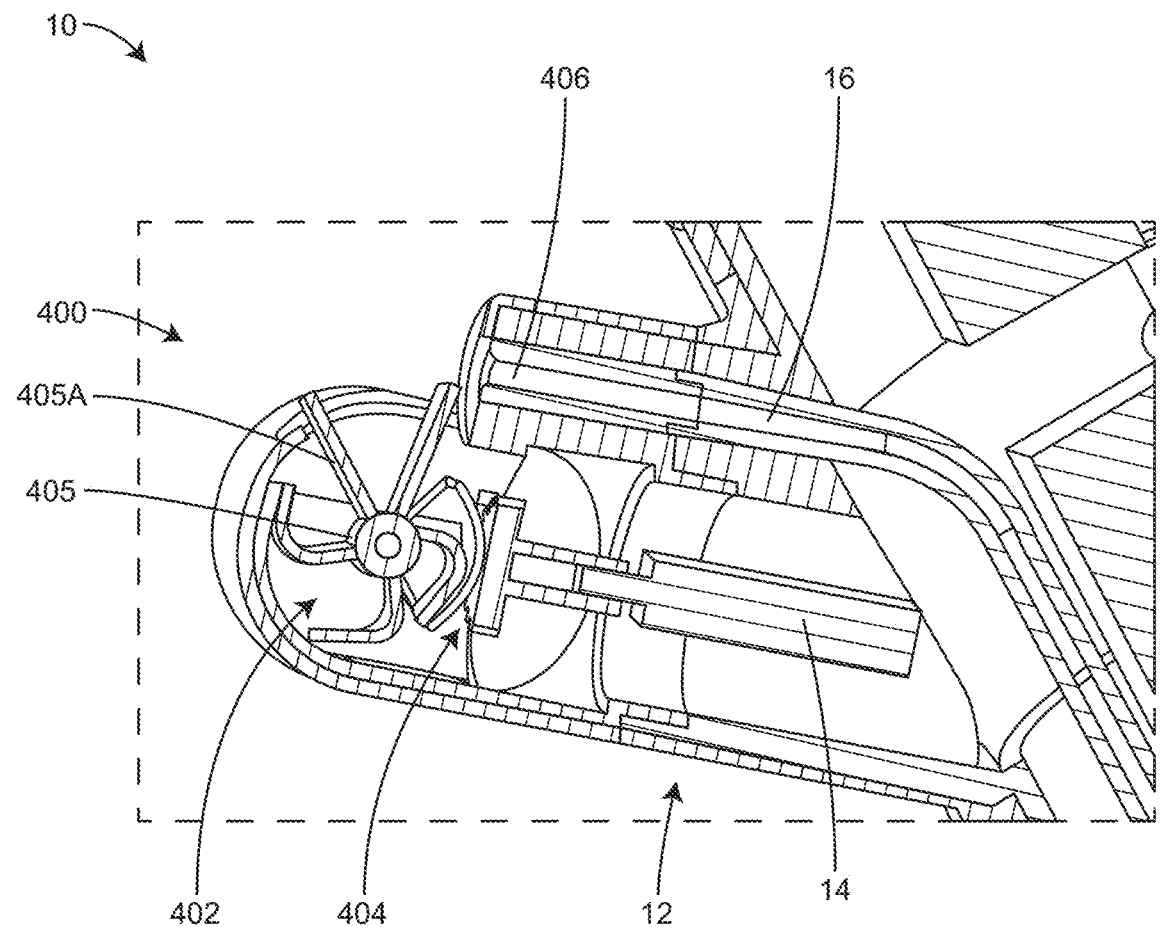
FIG. 5C is an enlarged view of the adult toy as shown in FIG. 5B.
Figure 5D:
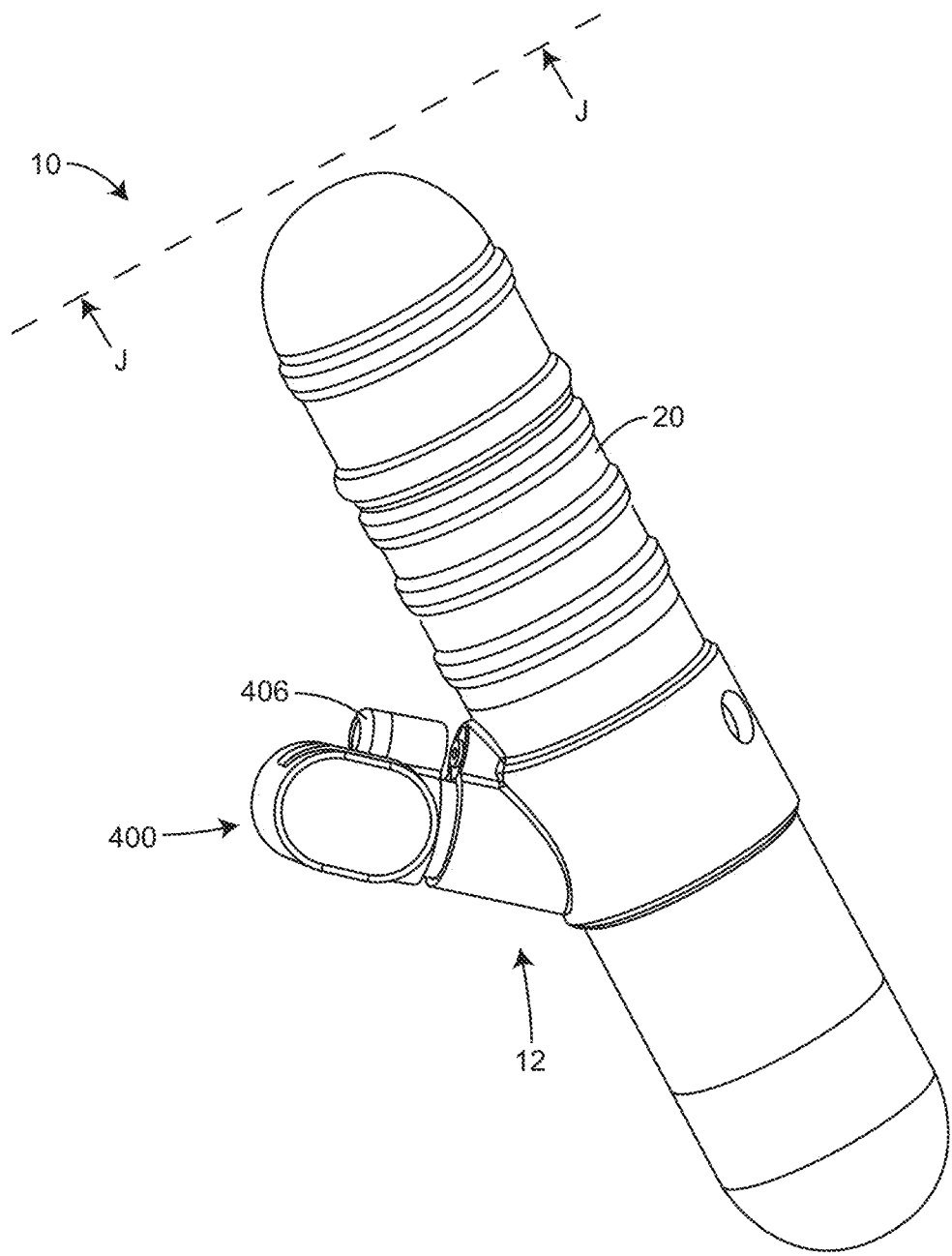
FIG. 5D is a partially exploded view of the adult toy of FIG. 5A.
Figure 5E:
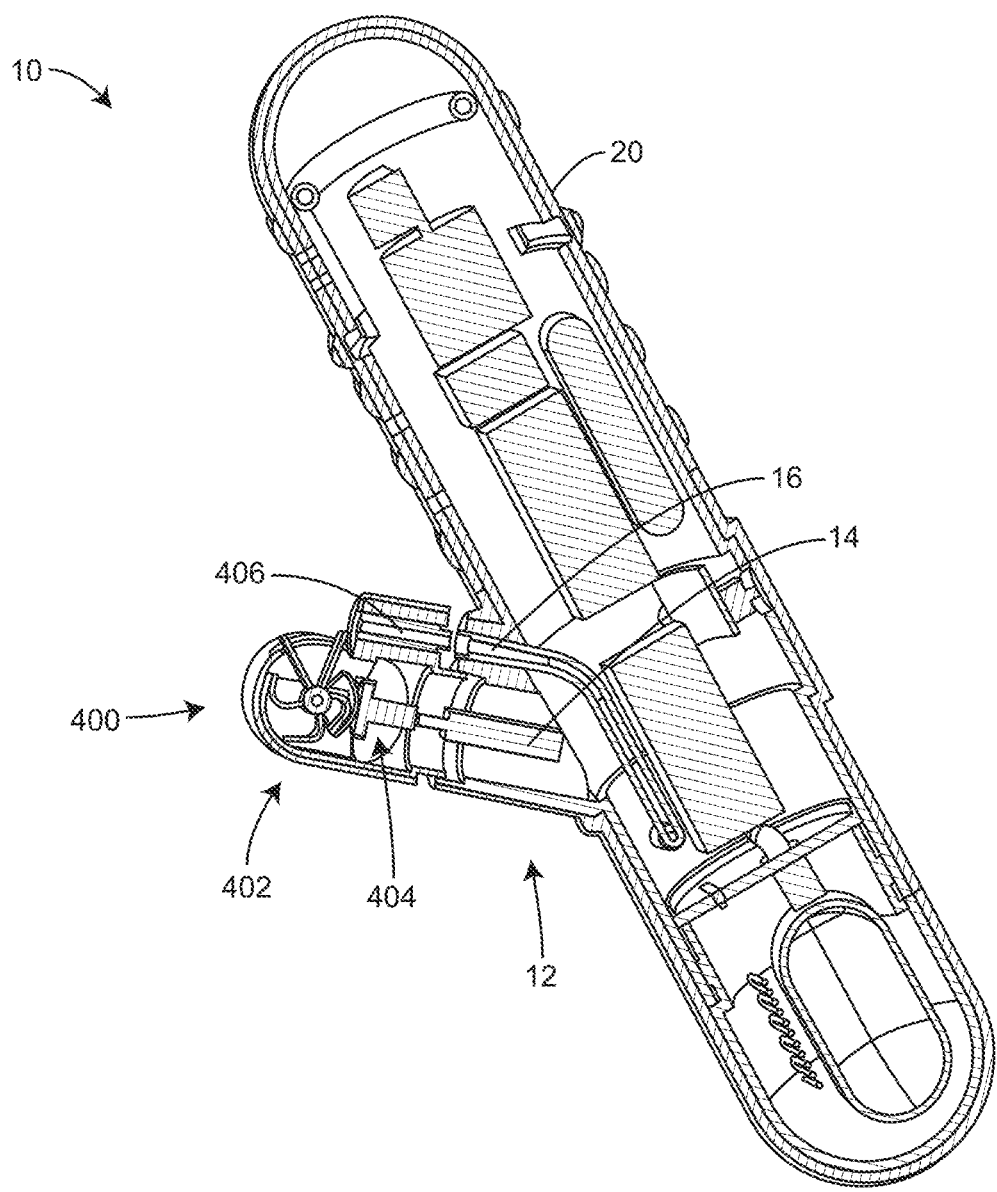
FIG. 5E is a cross-sectional view taken along line J-J in FIG. 5D.

As can be seen in FIGS. 1F to 1H, the adult toy 10 includes a capsule receiving portion 52 configured to receive the lubricant capsule 50 therewithin and a locking mechanism 70 configured to lock the lubricant capsule 50 within the cartridge receiving portion 52 by a locking action. The lubricant inlet port 30 is configured to be in fluid communication with the lubricant capsule 50 when the lubricant capsule 50 is positioned within the capsule receiving portion 52. The inlet port 30, the capsule receiving portion 52, and the locking mechanism 70 are configured such that the fluid communication between the lubricant capsule 50 and the lubricant inlet port is established during said locking action of the locking mechanism 70. The lubricant inlet port 30 and the locking mechanism 70 are so positioned, and even dimensioned and oriented, that the locking action causes the engagement of the lubricant inlet port 30 with the lubricant capsule 50 for establishing said fluid communication.

It is to be understood herein that although the adult toy 10 has been illustrated as having the features relating to the replaceability of operative heads, features relating to the lubricant being deliverable from two distant ports of the adult toy as well as the features relating to the establishment of fluid communication between the lubricant inlet port and the lubricant capsule during the locking action, the adult toy can be realized with any one set of these features. The adult toy 10 can be realized with only the features related to the establishment of fluid communication between the lubricant inlet port and the lubricant capsule during the locking action without the adult toy necessarily having the features related to the lubricant being deliverable from two distant ports of the adult toy and the features related to replaceability of the operative heads. In other words, the presently disclosed subject matter includes within its scope an adult toy having the features related to the establishment of fluid communication between the lubricant inlet port and the lubricant capsule during the locking action with replaceable or fixedly attached operative heads and the main head, or even with a single head, and/or even without the features related to the lubricant being deliverable from two distant ports. For instance, the adult toy 10, according to some examples, can include a single fixed or replaceable head including the features related to the establishment of fluid communication between the lubricant inlet port and the lubricant capsule during the locking action.

In the illustrated example, the adult toy 10 includes a connector section 54 to which the capsule receiving portion 52 is removably connected via the locking mechanism 70. The lubricant inlet port 30 and a first locking part 72 of the locking mechanism 70 are positioned at the connector section 54. A second part 74 of the locking mechanism is positioned at the cartridge receiving portion 52. When the capsule receiving portion 52, having the lubricant capsule 50 positioned therewithin, is connected to the connector section 54, the lubricant inlet port 30 engages the lubricant capsule 50 and the fluid communication is established, i.e., by the locking action between the first and the second parts 72 and 74 of the locking mechanism 70. The lubricant capsule 50 includes a pierceable portion 51 and is positioned in the capsule receiving portion such that the pierceable portion 51 faces the lubricant inlet port 30. The lubricant inlet port 30 has a conical end 31 configured to pierce the pierceable portion 51 when the lubricant capsule 50 is pressed thereon.

Although in the illustrated embodiment, the locking mechanism 70 is a bayonet lock, it is to be understood herein that the locking mechanism can be any other locking mechanism such as a snap fit lock or a press lock by virtue of dimensions of the cartridge receiving portion and the connector section.

As can be seen in FIGS. 1A to 1H, the adult toy 10 further includes a heating mechanism 80 configured to heat the lubricant in the lubricant capsule 50 before the lubricant is delivered to the user organs. It is to be understood herein that the lubricant can be delivered from any other lubricant source than the capsule 50. The lubricant is a cannabinoid extract and can include CBD oil or THC oil.

Although the adult toy 10 has been illustrated as having all the features described above in addition to the heating mechanism, it is to be understood that the adult toy 10 can be realized with only the features related to the heating mechanism without all or some of the features detailed above. In other words, the presently disclosed subject matter includes within its scope an adult toy having the features related to the heating mechanism without any, some, or all the features detailed above. For instance, the adult toy 10, according to some examples, can include a single fixed or replaceable head configured to deliver a lubricant therethrough and a heating mechanism for heating the lubricant prior to its delivery to the user, with or without some or all of the features detailed above. In some examples, the adult toy can be an adult sex soy for use by male users with the features related to the heating mechanism. One such example is described further below herein with reference to FIGS. 7A and 7B.

In the illustrated example, the lubricant is contained in the lubricant capsule 50 removably positioned within the cartridge receiving position 52. The heating mechanism 80 is configured to be activated during the locking action connecting the capsule receiving portion 52 to the connector section 54. In some examples, the heating mechanism 80 can be configured to be activated by a part of the locking action, and particularly half of the locking action, for example, at the instance of first contact between the capsule receiving portion 52 and the connector section 54. The heating mechanism 80 includes a heating element 82 positioned in the cartridge receiving portion 52 and connected thereto for being moved therewith. The heating mechanism 80 further includes a conductor element 84 positioned at the connector section 54 and electrically connected to a power source, which in the illustrated example is battery 90. When the capsule receiving portion 52 is moved towards the connector section 54 for connection therewith, the heating element 82 engages the conductor element 84 and this completes the electrical circuit required to activate the heating mechanism 80. The lubricant is thus heated prior to its delivery to the user.

In the illustrated example, the controller 60 is configured to control the operation of the heating mechanism including the activation of the heating mechanism and the temperature thereof. The adult toy 10, according to some examples, can include a sensor to sense whether the capsule receiving portion 52 includes the lubricant capsule 50 or not and indicate to the controller 60 when the capsule receiving portion 52 includes the lubricant capsule 50 so that the controller 60 enables activation of the heating mechanism 80 only when the capsule 50 is positioned in the capsule receiving portion 52. For instance, if the capsule receiving portion 50 is empty, the locking thereof with the connector section does not activate the heating mechanism 80 and this avoids wastage of power from the battery 90.

In all the examples described above, the battery 90 is configured to act as a power source for all the electrically operable components of the adult toy 10, for instance the main motor 24, the auxiliary motor 14, the pumping mechanism 40, and the sensor, etc. in some examples, the adult toy 10 can include different power sources for different electrically operable components. In some examples, the power source can be an external power source.

During use of the adult toy 10, the user can insert the main head 20 into the vagina and position the auxiliary head towards the clitoris, and trigger the adult toy by an actuator, which in the illustrated example is a switch S. The controller 60 sends commands to operate the motors 14 and 24, the pumping mechanism 40, and the heating mechanism 80 for simultaneously stimulating the vagina and clitoris of the user while dispensing the lubricant thereto for increased pleasure and/or relief. Thus, the main head 20 and the auxiliary heads constitute a stimulating member of the adult toy 10. The switch S can include controls for regulating the speed, patterns of operation, volume of the lubricant, duration of operation, etc. of the adult toy 10. In some examples, the motors 14 and 24, the pumping mechanism 40, and the heating mechanism 80 can be operated in one or more predetermined patterns for the purposes of maximum sexual pleasure, satisfaction and/or relief.

Reference is now made to FIGS. 2A-2D, 3A-3D, 4A-4D, and 5A-5D for describing various operative heads, which in the illustrated examples constitute the auxiliary heads, and operations thereof. FIGS. 2A to 2D illustrate an operative head 100 including an operational unit 102. The operative head 100 is configured to be attached to the auxiliary head port 12 of the adult toy 10 by the attaching action as described above, and the operational unit 102 is configured to be operationally coupled to the auxiliary motor 14 during that attaching action. The operative head 100 is a vibration head and the operational unit 102 is a vibrator unit 102. The vibrator unit 102 is configured to vibrate so as to perform the operation of vibration at the clitoris of the user. The vibrator unit 102 includes a vibrator motor 104 which operationally couples to the auxiliary motor 14 for performing the operation of the vibrator unit 102. The operative head 100, when attached to the head port 12, is configured to interact with the clitoris of the user during use of the adult toy 10, i.e., when the main head 20 is inserted into the vagina. The operative head 100 includes a lubricant port extension element 106, which in the illustrating example is a lubricant port extension pipe 106 that is configured to be connected, possibly in a leak-proof manner, to the lubricant delivery port 16 and deliver the lubricant therethrough at the clitoris. In some examples, the lubricant port extension pipe 106 can extend through the vibrator unit 102 for delivering the lubricant more precisely at the clitoris.

FIGS. 3A to 3D illustrate an operative head 200, which in the illustrated example is an auxiliary head 200 including an operational unit 202. The operative head 200 is configured to be attached to the auxiliary head port 12 of the adult toy 10 by the attaching action as described above, and the operational unit 202 is configured to be operationally coupled to the auxiliary motor 14 during that attaching action. The operative head 200 is a suction head and the operational unit 202 is a suction unit 202. The suction unit 202 is configured to perform the operation of suction at the clitoris of the user. The suction unit 202 includes a suction pump 204 which operationally couples to the auxiliary motor 14 for performing the operation of the suction unit 202. The operative head 200, when attached to the head port 12, is configured to interact with the clitoris of the user during use of the adult toy 10, i.e., when the main head 20 is inserted into the vagina. In some examples, the suction may include causing an under-pressure effect thereby repeatedly pulling a membrane associated with the clitoris of the user. The operative head 200 includes a lubricant port extension element 206, which in the illustrated example is a lubricant port extension pipe 206 that is configured to be connected, possibly in a leak-proof manner, to the lubricant delivery port 16 and deliver the lubricant therethrough at the clitoris. In some examples, the lubricant port extension pipe 206 can extend through the suction unit 202 for delivering the lubricant more precisely at the clitoris.

FIGS. 4A to 4D illustrate an operative head 300, which in the illustrated example is an auxiliary head 300 including an operational unit 302. The operative head 300 is configured to be attached to the auxiliary head port 12 of the adult toy 10 by the attaching action as described above, and the operational unit 302 is configured to be operationally coupled to the auxiliary motor 14 during that attaching action. The operative head 300 is a licking head and the operational unit 302 is a licking-mimicking unit 302. The licking-mimicking unit 302 includes a ball housing 303 housing a licking ball 305. The licking-mimicking unit 302 includes a licking motor arrangement 304 that operationally couples to the auxiliary motor 14 and is configured to move the ball housing 303 in a predetermined pattern, thereby moving the licking ball with respect to the clitoris for mimicking a licking action at the clitoris of the user during use of the adult toy 10, i.e., when the main head 20 is inserted into the vagina. In the illustrated example, the licking motor arrangement includes a licking motor extension element 304. The operative head 300 includes a lubricant port extension element 306, which in the illustrated example is a lubricant port extension pipe 306 that is configured to be connected, possibly in a leak-proof manner, to the lubricant delivery port 16 and deliver the lubricant therethrough at the clitoris. In some examples, the lubricant port extension pipe 306 can extend through the licking-mimicking unit 302 for delivering the lubricant more precisely at the clitoris.

FIGS. 5A to 5E illustrate an operative head 400, which in the illustrated example is an auxiliary head 400 including an operational unit 402. The operative head 400 is configured to be attached to the auxiliary head port 12 of the adult toy 10 by the attaching action as described above, and the operational unit 402 is configured to be operationally coupled to the auxiliary motor 14 during that attaching action. The operative head 400 is a licking head and the operational unit 402 is a licking-mimicking unit 402. The licking-mimicking unit 402 includes a licking motor arrangement 404 that is configured to rotate a licking element 405. The licking motor arrangement 404 operationally couples to the auxiliary motor 14 and is configured to rotate the licking element 405 about a rotation axis RA with respect to the clitoris for mimicking a licking action at the clitoris of the user during use of the adult toy 10, i.e., when the main head 20 is inserted into the vagina. The licking motor arrangement includes a licking motor and gear arrangement and the licking element 405 includes a licking wheel 405 having fins 405A that interact with the clitoris during operation thereof. In other examples, the licking element can be a ball or any element to cause a licking-mimicking effect at the clitoris. The operative head 400 includes a lubricant port extension element 406, which in the illustrated example is a lubricant port extension pipe 406 that is configured to be connected, possibly in a leak-proof manner, to the lubricant delivery port 16 and deliver the lubricant therethrough at the clitoris. In some examples, the lubricant port extension pipe 406 can extend through the licking-mimicking unit 402 for delivering the lubricant more precisely at the clitoris. In some examples, the lubricant port extension pipe 406 can be positioned so as to deliver the lubricant at the licking element 405 which is then rubbed onto the clitoris by the licking element 405.

Although the operative heads 100, 200, 300, and 400 have been described herein as being auxiliary heads, it is to be understood herein that the main head 20 can be any of these operative heads and can be configured to be attached (fixedly or removably) to the main port and perform corresponding operations.

It is to be understood herein the term interact with the clitoris includes within its scope touching/rubbing the clitoris, stimulating the clitoris, and/or causing any sensation at the clitoris.

The presently disclosed subject matter includes within its scope a kit including the adult toy 10 according to any one of the examples described above, and one or more operative heads according to any one of the examples described above.

Figure 6A:
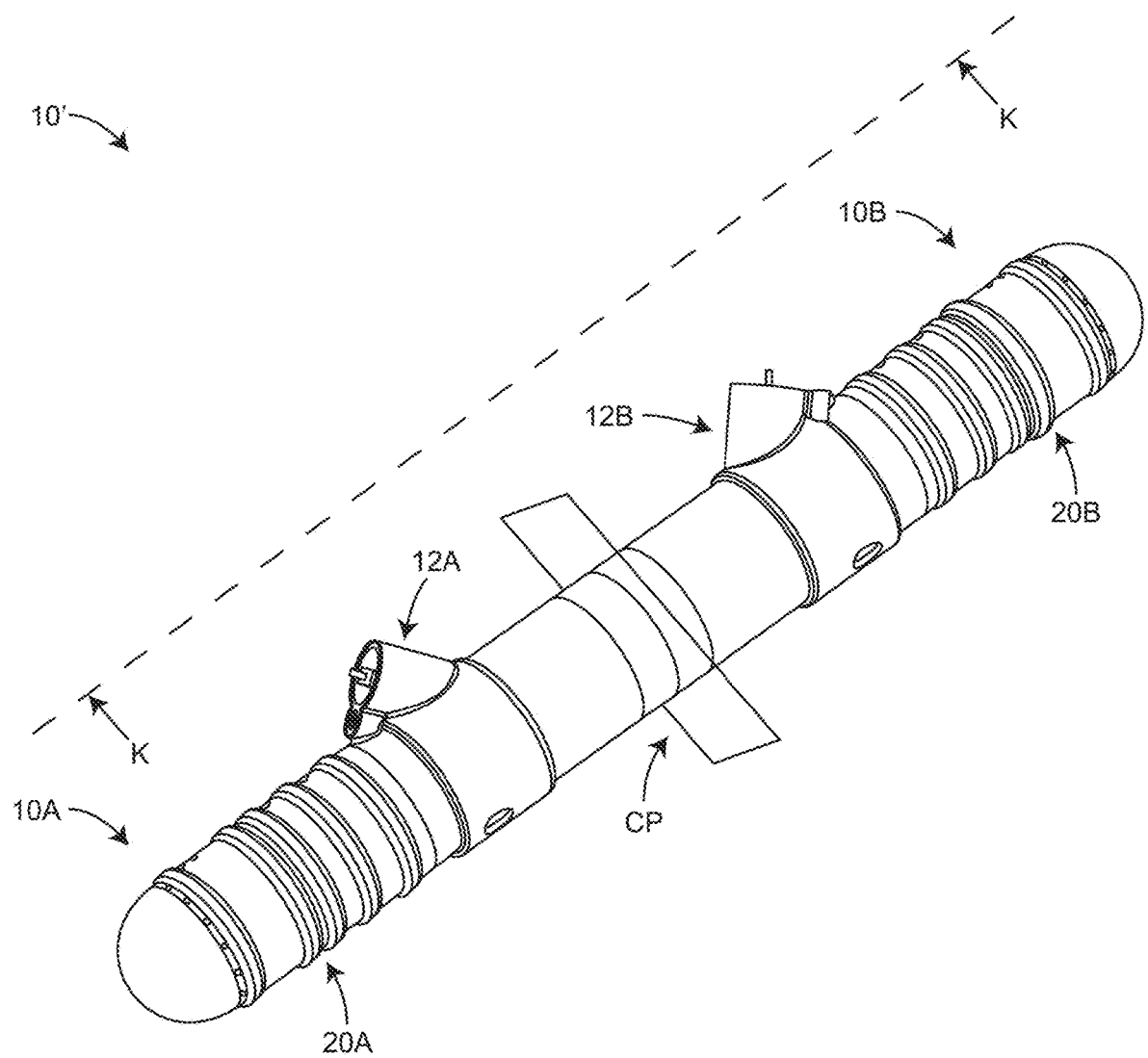
FIG. 6A is a perspective view of an adult toy according to another example of the presently disclosed subject matter.
Figure 6B:
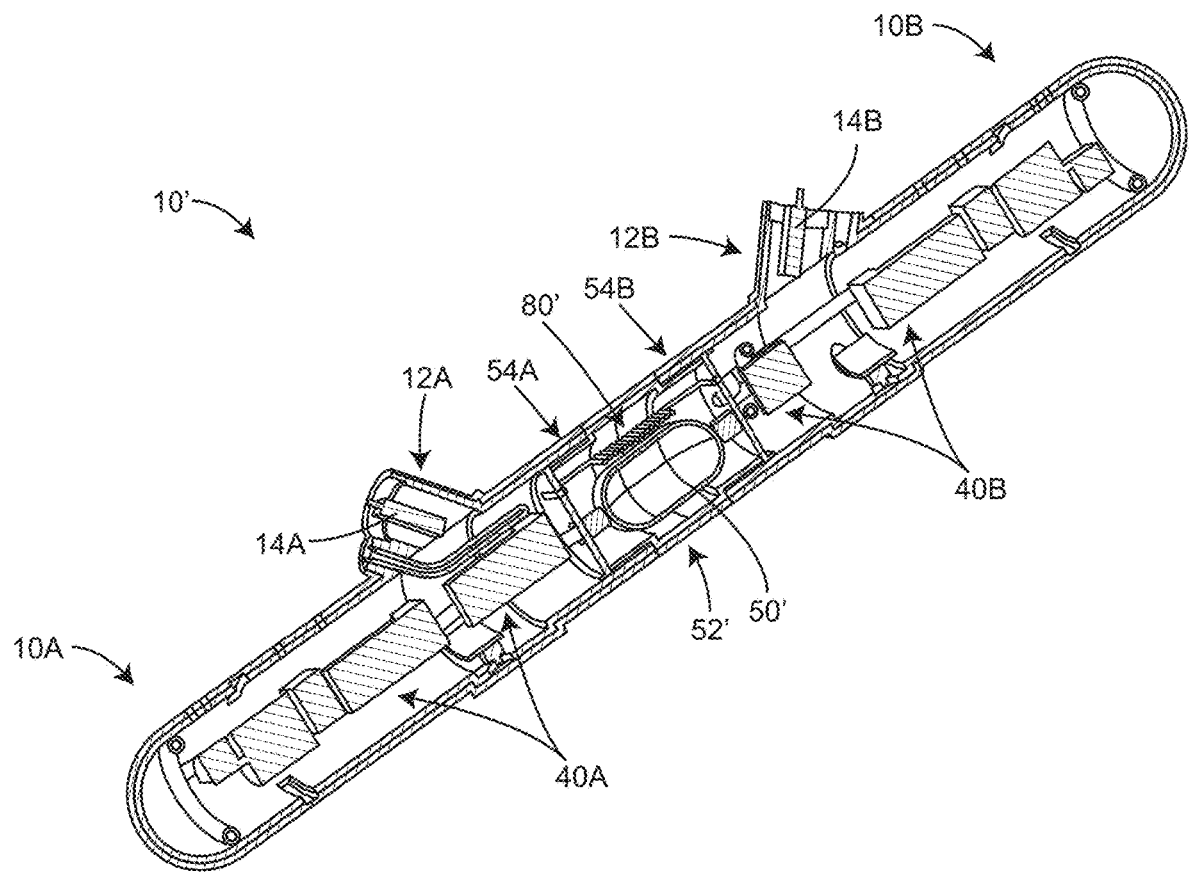
FIG. 6B is a cross-sectional view taken along line K-K in FIG. 6A.

Reference is now made to FIGS. 6A and 6B, which illustrates an adult toy 10' according to another example of the presently disclosed subject matter. The adult toy 10' is double sided adult toy primarily for use by a lesbian couple. For instance, the adult toy 10' includes two identical portions 10A and 10B symmetrically positioned across a central plane CP, each for use by either partner of the lesbian couple. Each of the two adult toy portions 10A and 10B have been illustrated as being identical to the adult toy 10 as described above including all of its features detailed above. However, it is to be understood herein that any of the two adult toy portions 10A and 10B can include some or all of the features of the adult toy 10 described above and can exclude others of its features. The adult toy portions 10A and 10B can be flexible and deformable with respect to each other, for example at the central plane CP for ease of use by the couple.

The adult toy 10' includes two head ports 12A and 12B, two motors 14A and 14B each associated with a corresponding head port, two main heads 20A and 20B and two pumping mechanisms 40A and 40B. All these components are similar in structure and operation to the corresponding components of the adult toy 10. The adult toy 10' includes a single lubricant capsule 50' positioned in a single capsule receiving portion 52' configured to be attached to both the adult toy portions 10A and 10B at their respective connector sections 54A and 54B, and be heated by a single heating mechanism 80'. Although, the adult toy 10' has been illustrated as having a single lubricant capsule, it is to be understood herein that in some examples, the adult toy 10' can have two lubricant capsules containing same or different lubricant. In some examples, the single capsule can have two separate portions each containing different or same lubricant. In some examples, the single capsule can be connected to a single lubricant inlet port having four pathways, two extending to each of the adult toy portions, one of those two for the corresponding main head, and the other one for the corresponding auxiliary head.

It is to be understood herein that the adult toy 10 (as described with respect to FIGS. 1A to 1H) can be configured such that it can be connected to another adult toy at its connector section to arrive at the adult toy 10' described above. For instance, the other adult toy can be identical (in structure and at least some of the features) to the adult toy 10. Thus, the adult toy 10 can be used as a stand-alone toy by a single user or can be retrofitted with another adult toy for use by a lesbian couple.

Figure 7A:
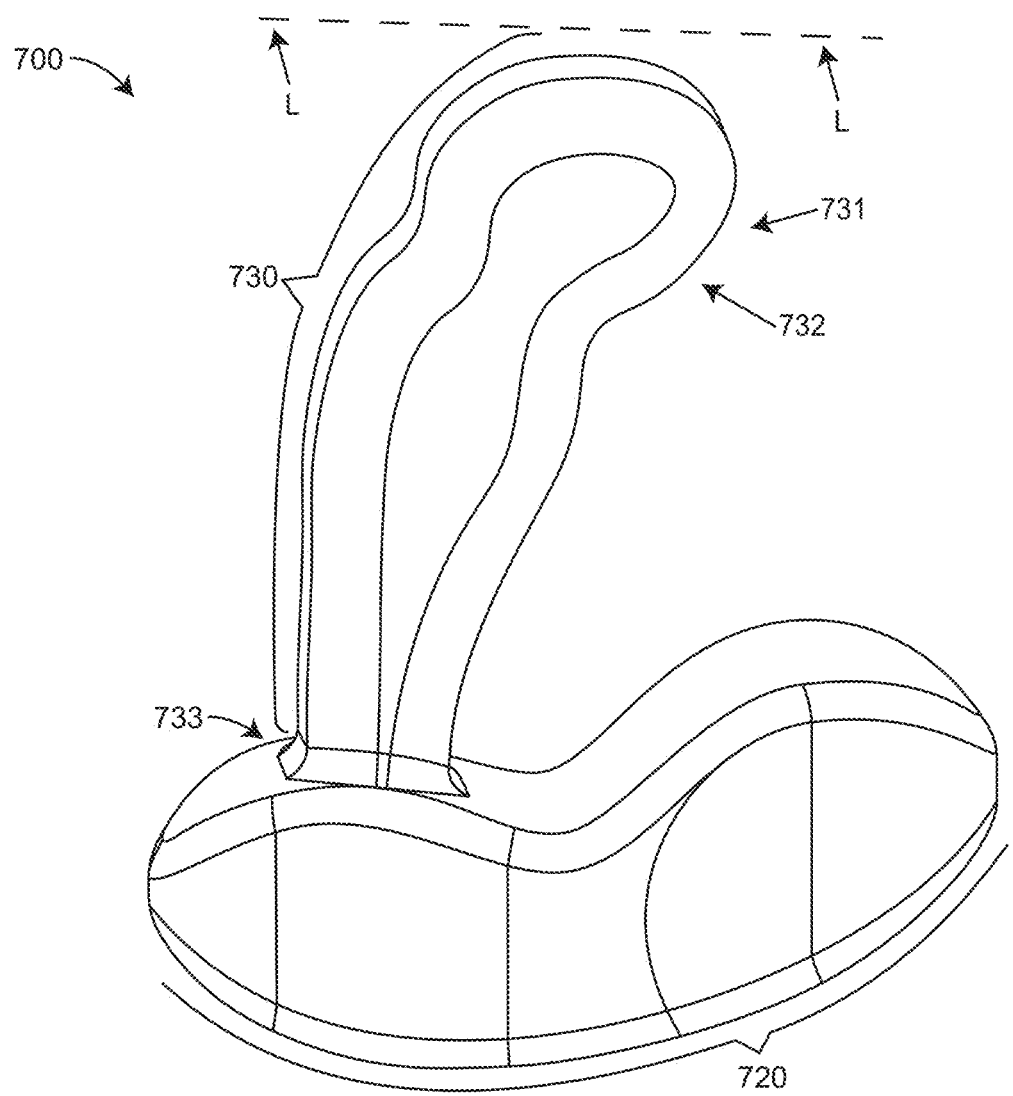
FIG. 7A is a perspective view of an adult toy according to yet another example of the presently disclosed subject matter.
Figure 7B:
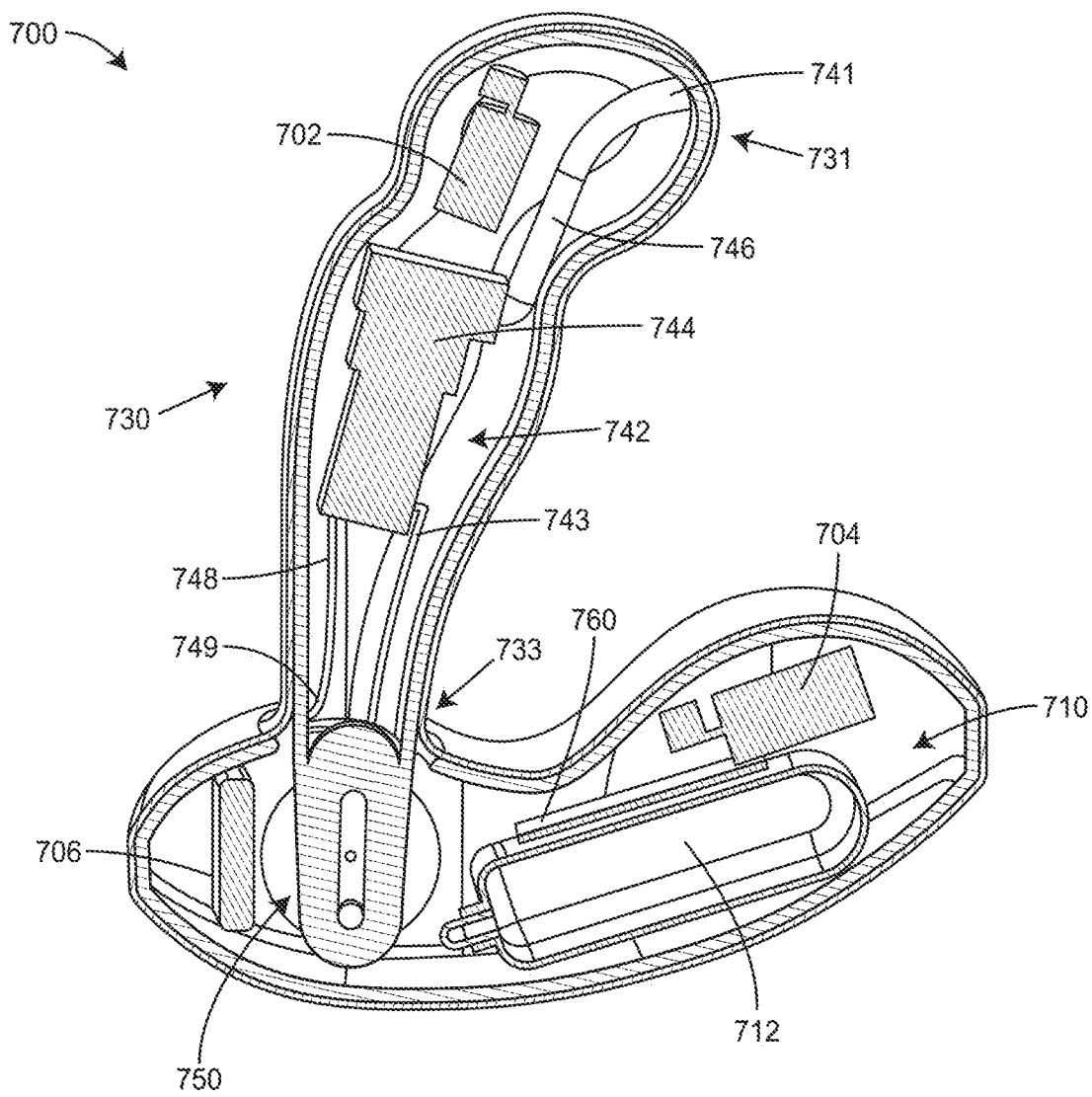
FIG. 7B is a cross-sectional view taken along line L-L in FIG. 7A.

Reference is now made to FIGS. 7A and 7B, which illustrates an adult toy 700 according to yet another example of the presently disclosed subject matter. The adult toy 700 is configured for delivering a cannabinoid extract lubricant to a user. The adult toy 700 includes a capsule receiving portion 710 configured for removably receiving therewithin a lubricant capsule 712 containing the cannabinoid extract lubricant. The adult toy 700 is configured to be used primarily by a male user. For instance, the adult toy 700 includes a proximal portion 720 configured to interact with testicles of the user and a distal portion 730 configured to be inserted into an anus of the user during use of the adult toy 700. The proximal portion 720 can be held by the user for inserting the distal portion 730 inside the anus. The shape of the adult toy 700 defined primarily by the orientation of the distal portion 730 with respect to the proximal portion 720 is such that during use of the adult toy 700, the distal portion stimulates the prostate, particularly the P-spot, inside the anus while the proximal portion 720 is positioned towards the testicles and stimulates the testicles of the user simultaneously. The distal portion 730 is inclined at an acute angle A2 with respect to the proximal portion 720 and has a bulging portion 732 at a distal end 731 thereof for the purpose of stimulating the P-spot.

The adult toy 700 further includes a lubricant delivery mechanism 740 configured to deliver said cannabinoid extract lubricant from the lubricant capsule 712 to the user. The lubricant mechanism 740 includes a lubricant extraction mechanism 742 in fluid communication with the lubricant capsule 712 via a lubricant extraction conduit 743 and configured to extract the cannabinoid extract lubricant therefrom. In the illustrated example, the lubricant extraction mechanism 742 includes a pumping mechanism 744, which particularly includes a peristaltic pump 744, configured to extract the cannabinoid extract lubricant from the lubricant capsule 712. The lubricant extraction mechanism 740 includes a first conduit 746 extending from the pumping mechanism 744 towards the distal end 731 of the distal portion 730, and a second conduit 748 extending from the pumping mechanism 744 towards a proximal end 733 of the distal portion 730. The first conduit 746 is fluidly connected to a first lubricant outlet port 747 positioned at the distal end 731 and configured to deliver, by the pumping action of the pump 744, the cannabinoid extract lubricant inside the anus of the user through the first lubricant port 747 and a corresponding opening (not shown) at the distal end 731. The second conduit 748 is fluidly connected to a second lubricant outlet port 749 positioned at the proximal end 733 and configured to deliver, by the pumping action of the pump 744, the cannabinoid extract lubricant at the entrance of the anus of the user through the second lubricant port 749 and a corresponding opening (not shown) at the proximal end 733, during use of the adult toy 700. In some examples, the pumping mechanism can include a valve configured to establish the fluid connection between the pumping mechanism and both the first and second conduits. The valve can be configured to selectively open and close the fluid communication with either of the conduits. It is to be understood herein that in some examples, the lubricant delivery mechanism can include separate pumping mechanisms for the first conduit and the second conduit and separate corresponding ports in the lubricant capsule for fluid connection thereto.

The adult toy 700 further includes a first vibrator motor 702 configured to move the distal portion 730, when the adult toy is in use. The first vibrator motor 702 is operationally coupled to a motor mechanism 750 of the adult toy configured to operate the first vibrator motor 702 to move the distal portion 730 with respect to the proximal portion 720 to stimulate the prostate of the user. The adult toy 700 further includes a second vibrator motor 704 configured to move the proximal portion 720, when the adult toy is in use. The second vibrator motor 704 can as well be operationally coupled to the motor mechanism 750 for being operated thereby for vibrating to stimulate the testicles of the user. In some examples, the first and the second vibrator motor 702 and 704 can constitute parts of a single vibration unit.

The adult toy further includes a heating mechanism 760 configured to heat the cannabinoid extract lubricant prior to its delivery to the user. The cannabinoid extract lubricant has medicinal effects for providing relief in prostate related problems, and heating the same significantly enhances the relief provided by the adult toy 700.

The adult toy 700 further includes a power source 706, which in the illustrated example is a battery 706 to provide the power to electrically operated components, such as the vibrator motors, the motor mechanism, pumping mechanism, and the heating mechanism, of the adult toy 700. The adult toy 700 further includes a controller (not shown) to independently or in coordination with each other, control the operation of the components of the adult toy 700, and is configured to be triggered by the user via an actuator (not shown).

Although the adult toy 700 has been illustrated as a male adult toy, it is to be understood that the presently disclosed subject matter includes within its scope an adult toy, to be used by a male, female, transgender, lesbian, gay, or bisexual user, configured for delivering a cannabinoid extract lubricant to a user, including a capsule receiving portion configured for removably receiving therewithin a lubricant capsule containing the cannabinoid extract lubricant. Such an adult toy can include a common adult toy being configured to be used with a lubricant capsule containing cannabinoid extract lubricant and to deliver said cannabinoid extract lubricant to the user, and in some examples, include a heating mechanism to heat the cannabinoid extract lubricant prior to its delivery. Further, it is to be understood that the presently disclosed subject matter includes within its scope a capsule containing cannabinoid extract lubricant and configured for use with such an adult toy.

In all of the examples, described above the cannabinoid extract lubricant can include CBD oil and/or THC oil.

Figure 8A:
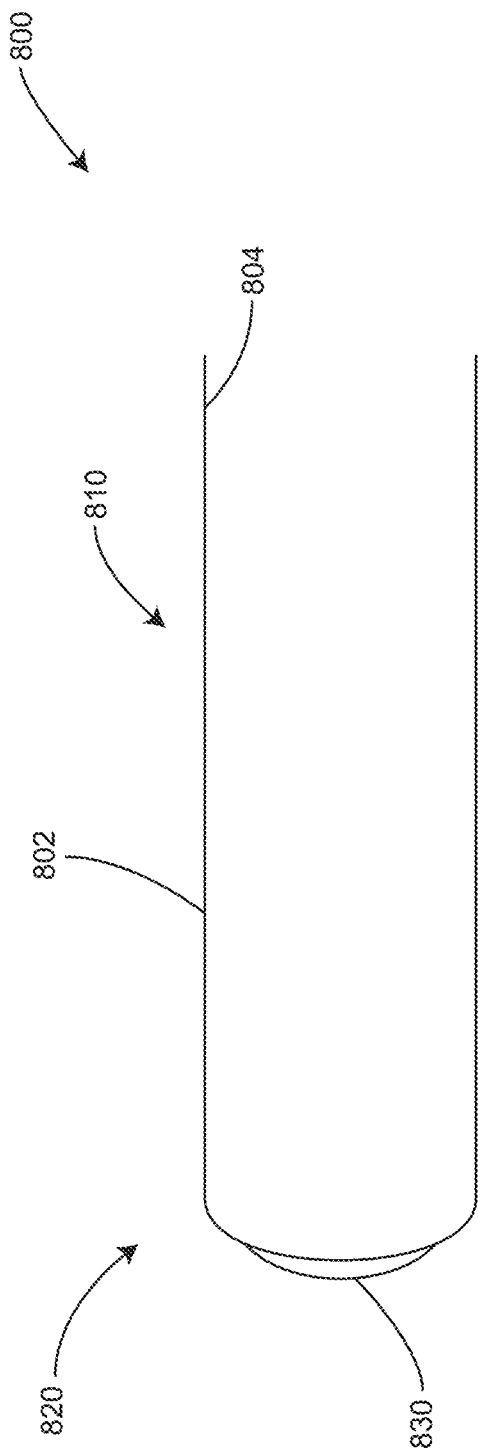
FIG. 8A is a schematic side view of a condom according to an example of the presently disclosed subject matter.
Figure 8B:
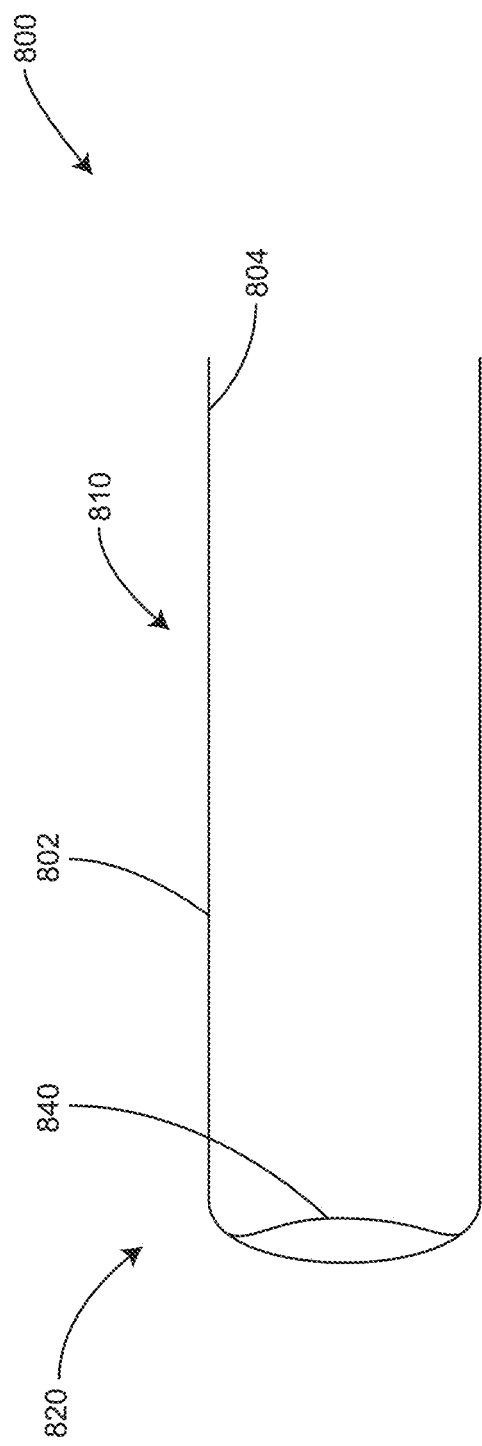
FIG. 8B is a schematic side view of a condom according to another example of the presently disclosed subject matter.
Figure 8C:
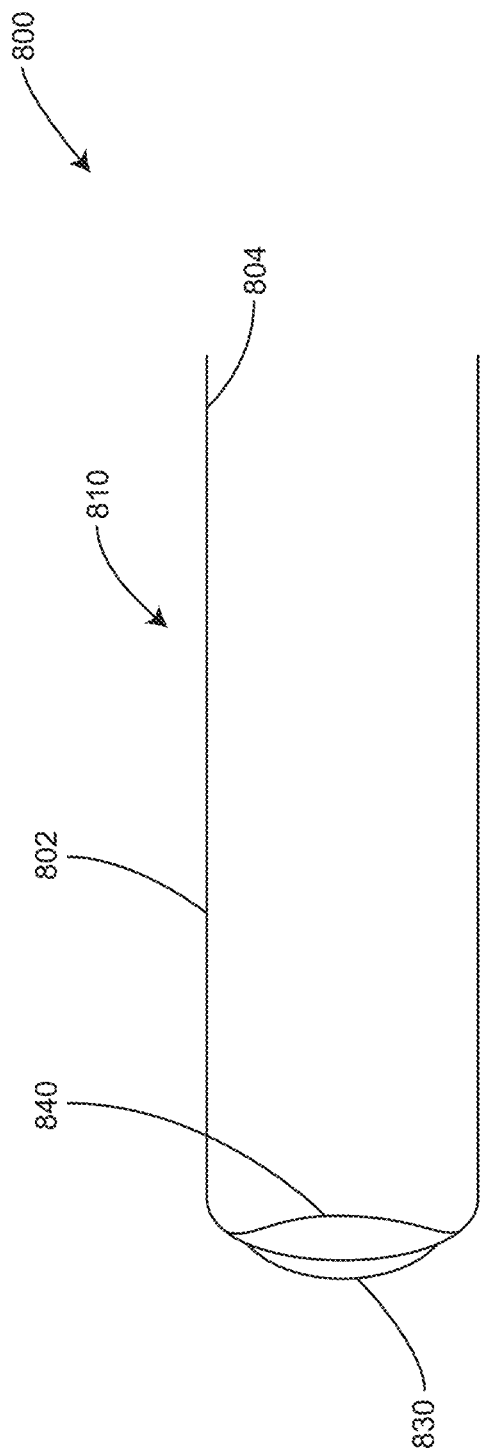
FIG. 8C is a schematic side view of a condom according to yet another example of the presently disclosed subject matter.

FIGS. 8A to 8C illustrate various examples of a condom 800 according to an aspect of the presently disclosed subject matter. The condom 800 includes a main condom portion 810 and a distal condom portion 820. According to the example illustrated in FIG. 8A, the condom 800 includes an external pocket 830 located at an external surface 802 of the condom and configured to hold a lubricant (for example, a sexually stimulating substance) and to selectively dispense the substance inside a vagina (or anus based on the use of the condom) of a user during use thereof.

According to the example illustrated in FIG. 8B, the condom 800 includes an internal pocket 840 located at an internal surface 804 of the condom and configured to hold a lubricant (for example, a sexually stimulating substance) and to selectively dispense the substance inside the condom (at the penis of a user wearing the condom) during use thereof.

According to the example illustrated in FIG. 8B, the condom 800 includes both the external pocket 830 and the internal pocket 840 configured serving their respective purposes as described above. The two pockets can include same or different lubricants.

The pockets 830 and 840 can be made of a material that could be at least partially permeable, disposable, tear able, pierceable, or combinations thereof. In some examples, the pockets 830 and 840 can be made up of substance that is configured to dissolve within the user body organ thereby releasing the sexually stimulating substance.

The condom 800 is configured to be used by a user in a manner condoms are generally known to be used and/or along with any of the adult toys 10, 10', and 700 described above, wherein the condom 800 can be placed over the portions of the adult toys configured to be inserted into sexual organ of the user. The condom 800 can be used as an alternative to or in addition to the lubricant capsules of the adult toys described above. The condom 800 can be used with any generally known adult toy adding thereto the functionality of the sexually stimulating substance and the capability of releasing the same during use.

According to all the examples, described above, the adult toys are externally covered by a covering member made up of silicone or a material including silicone to provide a feeling of smoothness, softness, and comfort to the user.

According to all the examples described above, the lubricant or the sexually stimulating substance can be cannabinoid extract, particularly including CBD or CBD oil. The cannabinoid extract includes THC oils.

The invention claimed is:

1. An adult toy comprising:
    a lubricant inlet port connectable to a lubricant source containing a lubricant to be delivered through the adult toy;
    a main conduit configured to dispense said lubricant from the lubricant inlet port through a main lubricant delivery port at an organ of a user of the adult toy;
    an auxiliary conduit configured to dispense said lubricant from the lubricant inlet port through an auxiliary lubricant delivery port at a second organ of the user of the adult toy at a location distant from a location at which the main lubricant delivery port dispenses the lubricant; and
    a pumping mechanism that pumps the lubricant from the lubricant inlet port through each of the main conduit and auxiliary conduit.

2. The adult toy according to claim 1, wherein the lubricant inlet port is a double one-way valve.

3. The adult toy according to claim 1, wherein the pumping mechanism comprises a first peristaltic pump configured to pump the lubricant from said lubricant inlet port through the main conduit.

4. The adult toy according to claim 3, wherein the pumping mechanism comprises a second peristaltic pump configured to pump the lubricant from said lubricant inlet port through the auxiliary conduit.

5. The adult toy according to claim 1, wherein the main lubricant delivery port is associated with a main head port of the adult toy, the main head port being configured for attaching thereto a main head insertable into a vagina of a user of the adult toy, said main lubricant delivery port being configured to deliver said lubricant through the main head inside the vagina.

6. The adult toy according to claim 1, wherein the auxiliary lubricant delivery port is associated with an auxiliary head port of the adult toy, the auxiliary head port being configured for removably attaching thereto one or more auxiliary heads, each auxiliary head being configured to perform one or more operations associated with a clitoris of a user of the adult toy.

7. The adult toy according to claim 6, wherein the auxiliary lubricant delivery port is configured for attaching thereto a lubricant port extension element of the corresponding auxiliary head for delivering therethrough the lubricant to the clitoris.

8. The adult toy according to claim 1, further comprising a controller configured for controlling the pumping mechanism.

9. The adult toy according to claim 4, further comprising a controller configured for controlling the pumping mechanism, wherein the controller is configured to operate the first and the second peristaltic pumps in coordination with each other.

10. The adult toy according to claim 4, further comprising a controller configured for controlling the pumping mechanism, wherein the controller is configured to operate the first and the second peristaltic pumps independently of each other.

* * * * *